United States Patent
Song et al.

(10) Patent No.: US 9,783,776 B2
(45) Date of Patent: Oct. 10, 2017

(54) YEAST HAVING IMPROVED PRODUCT PRODUCTIVITY AND METHOD OF PRODUCING PRODUCT

(71) Applicants: Samsung Electronics Co., Ltd., Suwon-si, Gyeonggi-do (KR); SNU R&DB Foundation, Seoul (KR)

(72) Inventors: Jiyoon Song, Seoul (KR); Jisook Hahn, Seoul (KR); Changduk Kang, Gwacheon-si (KR); Daehee Kim, Seoul (KR); Kwangmyung Cho, Gyeonggi-do (KR)

(73) Assignees: SAMSUNG ELECTRONICS CO., LTD., Suwon-si (KR); SNU R&DB FOUNDATION, Seoul (KR)

( * ) Notice: Subject to any disclaimer, the term of this patent is extended or adjusted under 35 U.S.C. 154(b) by 0 days.

(21) Appl. No.: 14/722,834

(22) Filed: May 27, 2015

(65) Prior Publication Data

US 2016/0024539 A1    Jan. 28, 2016

(30) Foreign Application Priority Data

Jul. 28, 2014    (KR) .................. 10-2014-0096012

(51) Int. Cl.

| | |
|---|---|
| *C12P 7/56* | (2006.01) |
| *C12P 7/06* | (2006.01) |
| *C12N 1/16* | (2006.01) |
| *C12N 1/19* | (2006.01) |
| *C12P 7/40* | (2006.01) |
| *C12N 9/02* | (2006.01) |
| *C12N 9/04* | (2006.01) |
| *C12N 9/88* | (2006.01) |

(52) U.S. Cl.
CPC ............ *C12N 1/16* (2013.01); *C12N 9/0006* (2013.01); *C12N 9/0008* (2013.01); *C12N 9/88* (2013.01); *C12P 7/06* (2013.01); *C12P 7/40* (2013.01); *C12P 7/56* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 7,405,068 B2 * | 7/2008 | van Maris | ............... C07C 51/44 435/254.21 |
| 2009/0053782 A1* | 2/2009 | Dundon | .................... C12P 7/56 435/139 |
| 2011/0039327 A1* | 2/2011 | Winkler | ................ C07K 14/37 435/254.21 |
| 2011/0045559 A1 | 2/2011 | Winkler et al. | |
| 2011/0104769 A1 | 5/2011 | Porro et al. | |

OTHER PUBLICATIONS

Schmidt et al., Std1 and Mth1 proteins interact with the glucose sensors to control glucose-regulated gene expression in Saccharomyces cerevisiae, Mol. Cell. Biol., 1999, 19, 4561-71.*

* cited by examiner

*Primary Examiner* — Robert Mondesi
*Assistant Examiner* — Todd M Epstein
(74) *Attorney, Agent, or Firm* — Leydig, Voit & Mayer, Ltd.

(57) ABSTRACT

A genetically modified yeast cell that is capable of consuming glucose at an increased rate and a method of efficiently producing pyruvate or pyruvate-derived products by using the yeast cell.

13 Claims, No Drawings

US 9,783,776 B2

YEAST HAVING IMPROVED PRODUCT PRODUCTIVITY AND METHOD OF PRODUCING PRODUCT

RELATED APPLICATION

This application claims the benefit of Korean Patent Application No. 10-2014-0096012, filed on Jul. 28, 2014, in the Korean Intellectual Property Office, the disclosure of which is incorporated herein in its entirety by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 62,028 Byte ASCII (Text) file named 719672_ST25.TXT created on May 1, 2015.

BACKGROUND

1. Field

The present disclosure relates to a yeast cell that consumes glucose at an increased rate compared to a parent cell and a method of efficiently producing pyruvate or pyruvate-derived products by using the yeast cell.

2. Description of the Related Art

Products such as organic acids and alcohols are widely used as building block materials in food, drug, and chemical industries. The materials are known to be produced from petroleum, and methods of producing the materials by using environment-friendly microorganisms are studied.

Methods of producing products such as organic acids by using microorganisms (e.g., yeast cells) may take a long time due to the need for fermentation and can incur great costs when one attempts to separate said products. Thus, more efficient and productive methods for producing products such as organic acids by using microorganisms are needed.

Approaches to increase the productivity of such methods depend on the assumption that variables such as acid stress limits the productivity of the microorganisms. Another focus of microorganism development is product formation which is enhanced as the result of increased enzyme activity. An example of an increased enzymatic activity may involve a central metabolic pathway such as glycolysis which provides intermediates necessary for product production.

Therefore, there is still a need for the production of enzymes having an increased productivity and a method of producing products by using the same.

SUMMARY

Provided is a genetically modified yeast cell comprising a deletion or disruption mutation of a gene encoding STD1.

Provided is a method of producing a glycolysis intermediate, a glycolysis intermediate-derived product, or a combination thereof. The method comprises culturing the genetically modified yeast cell in a cell culture medium, whereby the genetically modified yeast cell produces a glycolysis intermediate, a glycolysis intermediate-derived product, or a combination thereof; and recovering a glycolysis intermediate or a glycolysis intermediate-derived product from a culture solution.

Further provided is a method of providing a yeast cell with increased glycolysis, the method comprising deleting or disrupting a gene of a yeast cell that encodes STD1.

Related compositions and methods also are provided.

DETAILED DESCRIPTION

The term "activity decrease" or "decreased activity" of an enzyme or a polypeptide used herein denotes that the activity level of a genetically modified (i.e., genetically engineered) cell or an isolated enzyme or a polypeptide produced by a genetically modified cell is lower than an activity level measured in comparable cell of the same type that does not contain a given genetic modification, such as a parent cell, or the original polypeptide, or that no activity is shown. In other words, the term may refer to an activity of a polypeptide or enzyme which is decreased by about 10%, about 20%, about 30% or more, about 40% or more, about 50% or more, about 55% or more, about 60% or more, about 70% or more, about 75% or more, about 80% or more, about 85% or more, about 90% or more, about 95% or more, or about 100% in comparison with the same biological activity of the original polypeptide or enzyme which is not genetically modified (i.e., not genetically engineered), such as a polypeptide or enzyme of a cell which is not genetically engineered, e.g., a polypeptide or enzyme of a parent cell, or a wild-type polypeptide or enzyme. A polypeptide or enzyme having a decreased activity may be verified by using a method known to those of ordinary skill in the art. The activity decrease includes the situations where an enzyme is expressed but the enzyme exhibits decreased activity or no activity, or the case where a gene encoding an enzyme is not expressed or, even when the gene is expressed, the expression is lower than the expression of a gene encoding a polypeptide that is not genetically engineered or a gene encoding a wild-type polypeptide that is not genetically engineered.

The term "parent cell" used herein may refer to a cell that does not have a specific genetic modification that results in an increased or decreased protein (e.g., enzyme) activity and/or increased or decreased expression of a gene, polypeptide, enzyme, or a combination thereof in a genetically modified cell. The term "wild-type" polypeptide or polynucleotide may refer to a polypeptide or polynucleotide that does not have a specific genetic modification.

The decrease of enzyme production and/or enzymatic activity may be caused by a deletion or disruption of a gene encoding the enzyme. The term "deletion" or "disruption" used herein refers to mutation, substitution, or deletion of a part of or the whole gene or a part of or the whole regulatory region such as a promoter or a terminator of a gene, or insertion of at least one base group to a gene for preventing a gene from expression or for preventing an expressed enzyme from showing activity or making an expressed enzyme show a decreased activity level. The deletion or disruption of the gene may be achieved by gene manipulation such as homogenous recombination, mutation generation, or molecule evolution. When a cell includes a plurality of the same genes or at least two different polypeptide paralogous genes, one or more genes may be deleted or disrupted.

The term "activity increase" or "increased activity" of an enzyme, a polypeptide, or a protein used herein denotes that the activity level of a genetically modified (i.e., genetically engineered) cell or an enzyme or a polypeptide produced by a genetically modified cell is higher than an activity level measured in the same kind of comparable cell, parent cell, or the original polypeptide. In other words, the term may refer to an activity of a polypeptide or enzyme which is increased by about 5%, about 10%, about 15%, about 20%, about 30%, about 50%, about 60%, about 70%, or about 100% in comparison with the same biological activity of the original polypeptide or enzyme which is not genetically engineered, such as a polypeptide of a parent cell, or a wild-type polypeptide. A polypeptide having an increased activity may be verified by using a method known to those of ordinary skill in the art.

The activity increase of a polypeptide may be achieved by expression increase of a gene, a polypeptide (e.g., an enzyme) or increase of specific activity of a polypeptide. The expression increase may be caused by introduction of a polynucleotide encoding the polypeptide, by increase of the copy number of the polypeptide, or by mutation of a regulatory region of the polynucleotide. The mutation of a regulatory region of the polynucleotide may include a modification of an expression regulatory sequence of a gene. The regulatory sequence may be a promoter sequence or a transcription terminator sequence for expression of the gene. In addition, the regulatory sequence may be a sequence encoding a motif that may affect gene expression. The motif may be, for example, a secondary structure-stabilization motif, a RNA destabilization motif, a splice-activation motif, a polyadenylation motif, an adenine-rich sequence, or an endonuclease recognition site.

A polynucleotide which is introduced into a cell, or whose copy number is increased within a cell, may be endogenous or exogenous. An endogenous gene refers to a gene pre-existing in the genetic material of a host cell (e.g., native to the host cell). An exogenous gene refers to a gene which is introduced into a host cell by a method such as integration to a host cell genome. An introduced gene may be homologous or heterologous with respect to the host cell.

The term "copy number increase" may be an increase of copy number by the introduction of a gene or amplification of a gene, including increases in copy number caused by genetic engineering a cell to have a gene which is not preexisting in the cell. The introduction of a gene may be mediated by a vehicle such as a vector. The introduction may be a transient introduction in which the gene is not integrated to a genome or insertion of the gene into a genome. The introduction may be performed, for example, by introducing to the cell a vector to which a polynucleotide encoding a target polypeptide is inserted, and then replicating the vector in the cell or integrating the polynucleotide into the genome.

The term "gene" refers to a nucleic acid fragment expressing a specific protein and may include a coding region as well as regulatory sequences such as a 5'-non-coding sequence or a 3'-non-coding sequence. The regulatory sequences may include a promoter, an enhancer, an operator, a ribosome binding site, a polyA binding site, and a terminator region.

The term "heterologous" means "foreign," or "not native," (genetic material from a different strain or species), whereas the term homologous means "native" to a host cell (genetic material from the same strain or species).

The term "secretion" means transport of a material from the inside of a cell to a periplasmic space or an extracellular environment.

The term "organic acid" used herein refers to not only neutral organic acids but also negatively charged organic acids and salts thereof interchangeably. The organic acids may include acetic acid, lactic acid, pyruvate, and TCA cycle intermediate such as citric acid, itaconic acid, isocitric acid, oxalosuccinic acid, α-ketoglutaric acid, succinic acid, succinyl-CoA, fumaric acid, maleic acid, or oxaloacetic acid. For example, acetic acid is interchangeably used with acetate or a salt thereof.

The term "sequence identity" of a nucleic acid or a polypeptide used herein refers to a degree of similarity of base groups or amino acid residues between two aligned sequences, when the two sequences are aligned to match each other as best possible, at corresponding positions. The sequence identity is a value that is measured by aligning to an optimum state and comparing the two sequences at a particular comparing region, wherein a part of the sequence within the particular comparing region may be added or deleted compared to a reference sequence. A sequence identity percentage may be calculated, for example, by comparing the two sequences aligned within the whole comparing region to an optimum; obtaining the number of matched locations by determining the number of locations represented by the same amino acids of nucleic acids in both of the sequences; dividing the number of the matched locations by the total number of the locations within the comparing region (i.e., a range size); and obtaining a percentage of the sequence identity by multiplying 100 to the result. The sequence identity percent may be determined by using a common sequence comparing program, for example, BLASTN or BLASTP (NCBI), CLC Main Workbench (CLC bio), MegAlign™ (DNASTAR Inc).

In confirming many different polypeptides or polynucleotides having the same or similar function or activity, sequence identities at several levels may be used. For example, the sequence identities may include about 50% or greater, about 55% or greater, about 60% or greater, about 65% or greater, about 70% or greater, about 75% or greater, about 80% or greater, about 85% or greater, about 90% or greater, about 95% or greater, about 96% or greater, about 97% or greater, about 98% or greater, about 99% or greater, or 100%.

An aspect of an exemplary embodiment provides a yeast cell having a deletion or disruption mutation of a gene encoding STD1 and, optionally, MTH1. The yeast cell may be capable of consuming glucose at an increased glucose consumption rate in comparison with a cell that is not genetically modified/engineered to have a deletion or disruption of STD1. The glucose consumption may be a process of forming two molecules of pyruvate from one molecule of glucose by glycolysis. The yeast cell may have an increased productivity of glycolysis intermediates or glycolysis intermediate-derived materials in comparison with a cell that is not genetically engineered. "Production" as used herein refers to intracellular production glycolysis intermediates or glycolysis intermediate-derived materials or secretion after intracellular production glycolysis intermediates or glycolysis intermediate-derived materials. A cell that is not genetically engineered or a parent cell may be a cell that is not genetically engineered to have a decreased activity of STD1 or STD1 and MTH1. In addition, the cell that is not genetically engineered or the parent cell may be a cell that does not have a deletion or disruption mutation of STD1 gene or STD1 and MTH1 genes.

The term "derived materials" used herein may refer to materials that are formed from a specific material by a biosynthetic process. The term "glycolysis intermediate-derived materials" used herein may refer to materials that are formed from a glycolysis intermediate, for example, pyruvate, by a biosynthetic process. The term "biosynthetic process" used herein includes not only biosynthetic processes which naturally exist in a cell but also a biosynthetic process newly formed by an external introduction of a gene.

Specifically, the glycolysis intermediates may be glucose-6-phosphate (G6P), fructose-6-phosphate (F6P), fructose-1,6-biphosphate (FBP), dihydroxyacetone phosphate (DHAP), glyceraldehyde 3-phosphate (GAP), 1,3-bisphosphoglycerate, 3-phosphoglycerate, 2-phosphoglycerate, phosphoenolpyruvate, or pyruvate. The glycolysis intermediate-derived materials may be a DHAP-derived material, a GAP-derived material, or a pyruvate-derived material. The "DHAP-derived material" may be glyceol-3-phosphate (G3P), glycerol, a glycerol-derived product, or a combination thereof. The "pyruvate-derived material" may be ethanol, acetic acid, acetyl-CoA, lactate, a TCA cycle intermediate, a derived product thereof, or a combination thereof. The TCA cycle intermediate may be citric acid, itaconic acid, isocitric acid, oxalosuccinic acid, α-ketoglutaric acid, succinic acid, succinyl-CoA, fumaric acid, maleic acid, oxaloacetic acid, or a combination thereof. The TCA cycle intermediate-derived material may be succinyl-CoA, succinic semialdehye (SSA), 4-hydroxybutyrate, 4-hydroxybutyrate-CoA, 4-hydroxybutyrate aldehyde, 1,3-butanediol (1,3-BDO), 1,4-butanediol (1,4-BDO), butanol, or isobutanol. The yeast cell may include a gene encoding an enzyme that converts succinic acid to 1,4-BDO. The enzyme may be, for example, CoA-dependent succinate semialdehyde dehydrogenase, 4-hydroxybutyrate (4-HB) dehydrogenase, 4-hydroxybutyryl-CoA (4HB-CoA) transferase, aldehyde/alcohol dehydrogenase, or *Clostridium acetobutylicum* AdhE2.

The yeast cell may have a mutation such as deletion or disruption of a gene encoding STD1, MTH1, or a combination thereof. The yeast cell may be a cell in which a part of or the whole gene encoding MTH1, STD1, or a combination thereof, or a part of or the whole regulatory factor such as a promoter thereof or a terminator region thereof may be mutated, substituted, or deleted, or one or more base is inserted to the gene. The yeast cell may be a cell in which activity of STD1, MTH1, or a combination thereof is decreased in comparison with a cell that is not genetically engineered or a parent cell. The parent cell may be a cell that does not have a deletion or disruption mutation of a gene encoding STD1, MTH1, or a combination thereof.

STD1 may change expression of a glucose-related gene. STD1 may be a transcriptional repressor of a gene encoding hexose transporter (HXT-HXT). An HXT may refer to a protein such as an enzyme capable of translocating a hexose such as glucose or fructose over a plasma membrane. The hexose transporter may be, for example, HXT1, HXT2, HXT3, HXT4, HXT5, HXT6, HXT7, HXT8, HXT9, HXT10, HXT11, HXT12, HXT13, HXT14, HXT15, HXT16, HXT17, GAL1, SNF3, or RGT2. STD1 may be a protein interacting and functioning with MTH1 transcription repressor. STD1 may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 1. STD1 gene may have about 75% or more, about 80% or more, about 85% or more, about 90% or more, about 95% or more, about 96% or more, about 97% or more, about 98% or more, about 99% or more, or about 100% sequence identity with a nucleotide sequence of SEQ ID NO: 2.

MTH1 may be a transcriptional repressor for genes encoding HXT. MTH1 may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 3. MTH1 gene may have a nucleotide sequence of SEQ ID NO: 4. The MTH1 and STD1 genes may be derived from a yeast, for example, *S. cerevisiae*.

The yeast cell may be a strain belonging to *Saccharomyces*, *Zygosaccharomyces*, *Pichia*, *Kluyveromyces*, *Candida*, *Shizosaccharomyces*, *Issachenkia*, or *Hansenula*. A strain belonging to *Saccharomyces* may be, for example, *S. cerevisiae*, *S. bayanus*, *S. boulardii*, *S. bulderi*, *S. cariocanus*, *S. cariocus*, *S. chevalieri*, *S. dairenensis*, *S. ellipsoideus*, *S. eubayanus*, *S. exiguus*, *S. florentinus*, *S. kluyveri*, *S. martiniae*, *S. monacensis*, *S. norbensis*, *S. paradoxus*, *S. pastorianus*, *S. spencerorum*, *S. turicensis*, *S. unisporus*, *S. uvarum*, or *S. zonatus*.

The yeast cell may be a cell in which the activity of an enzyme utilized in a pathway for synthesizing a pyruvate-derived material from pyruvate, and the activity an enzyme utilized in a pathway for synthesizing glycerol from DHAP or a glycerol-derived material from glycerol are increased. The pathway for synthesizing glycerol from DHAP may include G3P dehydrogenase (GPDH) which catalyzes a reaction of converting DHAP and NADH to G3P and NAD$^+$, and G3Pase which catalyzes a reaction of converting G3P to glycerol to Pi.

The "pyruvate-derived material" is described above. The increase in enzyme activity or the production of an organic product (e.g., a pyruvate-derived material) may be caused by an increase of the expression of a polynucleotide encoding the enzyme. The yeast cell may be cell in which the activity of an enzyme converting pyruvate to lactate or the activity of an enzyme of a pathway for converting pyruvate to ethanol is increased. The increase in enzyme activity or the production of an organic product (e.g., a pyruvate-derived material) may be caused by an increase of the expression of a polynucleotide encoding an enzyme converting pyruvate to lactate or the expression of an enzyme of a pathway for converting pyruvate to ethanol. A polynucleotide encoding an enzyme converting pyruvate to lactate may encode an enzyme classified as EC 1.1.1.27 or EC 1.1.1.28. An enzyme of a pathway for converting pyruvate to ethanol may be at least one of pyruvate decarboxylase or alcohol dehydrogenase (ADH). Pyruvate decarboxylase may be an enzyme classified as EC 4.1.1.1. ADH may be an enzyme classified as EC. 1.1.1.2.

Also, in the genetically modified yeast cell, the activity of a polypeptide that converts pyruvate to acetaldehyde, a polypeptide that converts lactate to pyruvate, a polypeptide that converts DHAP to G3P, or a combination thereof may be inactivated or decreased in comparison with a cell that is not genetically engineered or a parent cell. The genetically modified yeast cell may have a deletion or disruption mutation of a gene encoding a polypeptide that converts pyruvate to acetaldehyde, a polypeptide that converts lactate to pyruvate, a polypeptide that converts DHAP to G3P, or a combination thereof. The genetically modified yeast cell may be capable of producing lactate. In some embodiments, the activity of a pathway in the yeast cell responsible for inhibiting or disrupting the flow of metabolites to lactate may be inactivated or decreased. Alternatively or in addition, in the yeast cell, the activity of a pathway facilitating or helping a flow of metabolites to lactate may be increased.

When the yeast cell is for producing lactate, in the yeast cell, the activity of a polypeptide that converts pyruvate to acetaldehyde may be inactivated or decreased. The polypeptide that converts pyruvate to acetaldehyde may be an enzyme classified as EC 4.1.1.1. The polypeptide converting pyruvate to acetaldehyde may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 5. The gene encoding the polypeptide converting pyruvate to acetaldehyde may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 5. The gene may be pdc1 encoding pyruvate decarboxylase (PDC). In the yeast cell, the activity of alcohol dehydrogenase converting acetaldehyde to ethanol may also be inactivated or decreased. The alcohol dehydrogenase may be NADH-dependent. The pdc1 gene may have a nucleotide sequence of SEQ ID NO: 8.

In the yeast cell, the activity of a polypeptide that converts lactate to pyruvate may be inactivated or decreased. The polypeptide converting lactate to pyruvate may be a cytochrome c-dependent enzyme. The polypeptide converting lactate to pyruvate may be a lactate cytochrome-c oxydoreductase (CYB2). The lactate cytochrome c-oxydoreductase may be an enzyme classified as EC 1.1.2.4 acting on D-lactate or EC 1.1.2.3 acting on L-lactate. The polypeptide converting lactate to pyruvate may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 6. The gene encoding the polypeptide converting lactate to pyruvate may be an enzyme classified as EC 1.1.2.4 acting on D-lactate or EC 1.1.2.3 acting on L-lactate. The gene encoding the polypeptide converting lactate to pyruvate may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 6. The cyb2 gene may have a nucleotide sequence of SEQ ID NO: 9.

In the yeast cell, the activity of a polypeptide that converts DHAP to glycerol-3-phosphate may be inactivated or decreased. The polypeptide converting DHAP to glycerol-3-phosphate, which is cytosolic glycerol-3-phosphate dehydrogenase (GPD), may be an enzyme catalyzing reduction of DAHP to glycerol-3-phosphate by using oxidation of NADH to $NAD^+$. The GPD may belong to EC 1.1.1.8. The GPD may have about 75% or more, about 80% or more, about 85% or more, about 90% or more, about 95% or more, about 96% or more, about 97% or more, about 98% or more, about 99% or more, or about 100% sequence identity with an amino acid sequence of SEQ ID NO: 7. The gene encoding the GPD may be an enzyme classified as EC 1.1.1.8. The gene encoding the polypeptide converting lactate to pyruvate may have about 75% or more, about 80% or more, about 85% or more, about 90% or more, about 95% or more, about 96% or more, about 97% or more, about 98% or more, about 99% or more, or about 100% sequence identity with a nucleotide sequence encoding an amino acid sequence of SEQ ID NO: 7. The GPD gene may have a nucleotide sequence of SEQ ID NO: 10.

In the yeast cell, the activity of converting pyruvate to lactate may be increased. The increase of the activity of converting pyruvate to lactate may be achieved by introduction and expression increase of a gene encoding a polypeptide that converts pyruvate to lactate. The expression increase may be caused by increase of copy number of a gene or by mutation of a regulatory region of the gene. Increase of the gene may be caused by amplification of an endogenous gene or by introduction of an exogenous gene. The mutation of a regulatory region of the gene may be caused by mutation of a regulatory region of an endogenous gene. The exogenous gene may be homogenous or heterogenous.

The polypeptide converting pyruvate to lactate may be lactate dehydrogenase (LDH). The LDH may catalyze conversion of pyruvate to lactate. The LDH may be an NAD (P)-dependent enzyme acting on L-lactate or D-lactate. The NAD(P)-dependent enzyme may be an enzyme classified as EC 1.1.1.27 acting on L-lactate or EC 1.1.1.28 acting on D-lactate.

A polynucleotide encoding the lactate dehydrogenase may be derived from bacteria, yeast, fungi, mammals, or reptiles. The polynucleotide may encode LDH of at least one selected from *Pelodiscus sinensis japonicus, Ornithorhynchus anatinus, Tursiops truncatus, Rattus norvegicus*, and *Xenopus laevis*. The LDH derived from *Pelodiscus sinensis japonicus*, the LDH derived from *Ornithorhynchus anatinus*, the LDH derived from *Tursiops truncatus*, and the LDH derived from *Rattus norvegicus* may have an amino acid sequence of SEQ ID NOs: 11, 12, 13, and 14, respectively. The LDH may have about 75% or more, about 80% or more, about 85% or more, about 90% or more, about 95% or more, about 96% or more, about 97% or more, about 98% or more, about 99% or more, or about 100% sequence identity with amino acid sequences of SEQ ID NOs: 11, 12, 13, and 14, respectively. The gene encoding the LDH may have about 75% or more, about 80% or more, about 85% or more, about 90% or more, about 95% or more, about 96% or more, about 97% or more, about 98% or more, about 99% or more, or about 100% sequence identity with a nucleotide sequence encoding amino acid sequences of SEQ ID NOs: 11, 12, 13, and 14, respectively. The gene may have a nucleotide sequence of SEQ ID NO: 15.

A polynucleotide encoding the LDH may be a vector including an LDH derived from bacteria, yeast, fungi, mammals, or reptiles. The vector may include a replication origin, a promoter, a polynucleotide encoding a lactate dehydrogenase, and a terminator. The replication origin may include a yeast autonomous replication sequence (ARS). The yeast ARS may be stabilized by a yeast centrometric sequence (CEN). The promoter may be selected from the group consisting of a CYC promoter, a TEF promoter, a GPD promoter, and an ADH promoter. The CYC promoter, TEF promoter, GPD promoter, and ADH promoter may be, each respectively, have nucleotide sequences of SEQ ID NO: 16, 17, 18, and 19. The terminator may be selected from the group consisting of phosphoglycerate kinase 1 (PGK1), cytochrome c transcription (CYC1), and GAL1. The CYC1 terminator may have a nucleotide sequence of SEQ ID NO: 20. The vector may further include a selection marker.

A polynucleotide encoding lactate dehydrogenase may be included in a genome of yeast cell. When a polynucleotide encoding lactate dehydrogenase functions for production of active proteins in a cell, the polynucleotide is considered "functional" in a cell. A polynucleotide encoding lactate dehydrogenase is specific in production of L-LDH or D-LDH, and thus a yeast cell including the polynucleotide encoding lactate dehydrogenase may produce an L-lactate enantiomer, a D-lactate enantiomer, or a salt thereof.

The yeast cell may include a polynucleotide that encodes one LDH or polynucleotides that encode a plurality of copies of LDH. The polynucleotides that encode a plurality of copies of LDH may encode, for example, about 1 to about 8, about 1 to about 7, about 1 to about 6, about 1 to about 5, about 1 to about 4, or about 1 to about 3 copies of LDH. When the yeast cell includes the polynucleotides that encode a plurality of copies of LDH, each of the polynucleotides may be a copy of the same polynucleotide or may include a copy of a polynucleotide that encodes at least two different LDHs. A plurality of copies of a polynucleotide encoding exogenous LDH may be included in the same locus or in multiple loci within a host cell's genome.

In addition, the yeast cell may be *S. cerevisiae* in which the activity of a polypeptide that converts pyruvate to acetaldehyde, a polypeptide that converts lactate to pyruvate, a polypeptide that converts DHAP to G3P, or a combination thereof is inactivated or decreased, and the activity of a polypeptide that converts pyruvate to lactate is increased. In addition, in the yeast cell, the activity of a polypeptide catalyzing conversion of G3P to glycerol, a polypeptide catalyzing conversion of acetaldehyde to ethanol, or a combination thereof may be inactivated or decreased. The *S. cerevisiae* may be a KCTC 12415BP strain in which STD1 gene or both of STD1 gene and MTH1 gene are deleted.

The yeast cell may be capable of producing lactate, and may further include a polypeptide having the activity of converting lactate to another product. The yeast cell may further include a gene encoding a polypeptide having the activity of converting lactate to another product, wherein the polypeptide may be expressed by the gene. A polypeptide having the activity of converting lactate to another product may be, for example, an enzyme catalyzing conversion of lactate to lactyl-CoA or an enzyme catalyzing a reaction of polymerizing lactyl-CoA with lactyl-CoA or another monomer to form homopolylactate or a lactate-containing copolymer. An enzyme catalyzing conversion of lactate to lactyl-CoA and an enzyme catalyzing a reaction of polymerizing lactyl-CoA with lactyl-CoA or another monomer may be CoA-transferase, for example, a genetically engineered *Clostridium propionicum* propionate CoA transferase ($Pct_{cp}$), and *Pseudomonas* sp. MBEL 6-19 polyhydroxyalkanoate (PHA synthase 1 ($PhaC1_{Ps6-19}$), respectively (See Teak Ho Yang et al., Biotechnology and Bioengineering, Vol. 105, No. 1, Jan. 1, 2010, the disclosure of which is incorporated herein by reference).

The yeast cell may be a *Saccharomyces* strain in which STD1 gene or both of STD1 gene and MTH1 gene are deleted. The *Saccharomyces* strain may be *Saccharomyces cerevisiae*, for example, *Saccharomyces cerevisiae* CEN. PK2-1C.

Another aspect of an exemplary embodiment provides a method of producing a glycolysis intermediate or a glycolysis intermediate-derived product, wherein the method includes culturing an embodiment of the genetically engineered yeast cell described above in a cell culture medium, whereby the yeast cell produces a glycolysis intermediate or a glycolysis intermediate-derived product; and recovering a glycolysis intermediate or a glycolysis intermediate-derived product from a culture solution.

The culturing may be performed in a culture medium including a carbon source, for example, glucose. The medium used in yeast cell culturing may be any general medium appropriate for growth of a host cell such as a minimal medium or a complex medium including an appropriate supplement.

The medium used in the culturing may be a medium capable of satisfying specific yeast cell requirements. The medium may be a medium selected from the group consisting of a carbon source, a nitrogen source, a salt, a trace element, and a combination thereof.

To obtain pyruvate or a pyruvate-derived product, for example, lactate from the genetically engineered yeast cell, the culturing conditions may be appropriately controlled. The cell is cultured under aerobic conditions for growth. Under the aerobic conditions, the dissolved oxygen (DO) concentration may be about 20 v/v % or higher, for example, from about 20 to about 100 v/v %, from about 20 to about 80 v/v %, from about 20 to about 60 v/v %, from about 20 to about 40 v/v %, or from about 20 to about 30 v/v %. Then, for producing pyruvate or a pyruvate-derived product, for example, lactate, the cell may be cultured under microaerobic conditions, for example, at a DO concentration of about 2 v/v % or lower, for example, from about 0.001 to about 2 v/v %, from about 0.005 to about 2 v/v %, from about 0.01 to about 2 v/v %, from about 0.05 to about 2 v/v %, from about 0.1 to about 2 v/v %, from about 0.5 to about 2 v/v %, from about 1 to about 2 v/v %, or from about 1.5 to about 2 v/v %.

The term "culturing condition" refers to a condition for yeast cell culturing. The culturing condition may be, for example, a condition of a carbon source, a nitrogen source, or oxygen used by a yeast cell. A carbon source which may be used by a yeast cell includes a monosaccharide, a disaccharide, a polysaccharide, and others. The carbon source may be an assimilable sugar. An assimilable sugar may be a hexose or a pentose. Specifically, glucose, fructose, mannose, galactose or others may be used as the carbon source. A nitrogen source which may be used by a yeast cell is an organic nitrogen compound, or an inorganic nitrogen compound. Oxygen conditions for culturing a yeast cell may be anaerobic conditions having a normal oxygen partial pressure, low-oxygen conditions including oxygen from about 0.1% to about 10%, for example, from about 0.1% to about 8%, from about 0.1% to about 6%, from about 0.1% to about 4%, from about 0.1% to about 2%, from about 0.1% to about 1%, from about 1% to about 10%, from about 1% to about 8%, from about 1% to about 6%, from about 2% to about 10%, from about 4% to about 10%, from about 6% to about 10%, from about 8% to about 10%, from about 2% to about 8%, or from about 2% to about 6% in the atmosphere, or anaerobic conditions including no oxygen. A metabolic pathway may be adjusted according to a carbon source and a nitrogen source which may be actually used by a microorganism.

Pyruvate or a pyruvate-derived product, for example, lactate may be separated from the culture solution by a common method known in this art. The recovery or separation method may be centrifugation, filtration, ion-exchange chromatography, or crystallization. For example, the culture solution may be centrifuged at a low speed to remove biomass and the resulting supernatant may be separated by ion-exchange chromatography.

The recovery may be recovery from a cell, a culture medium, or from both a cell and a culture medium.

Hereinafter, the present invention will be described in further detail with reference to examples. However, these examples are for illustrative purposes only and are not to be construed to limit the scope of the present invention.

Example 1. Effect of Activity Decrease of STD1 Gene, MTH1 Gene, or MTH1 and STD1 Genes in Yeast Cell In Example 1, STD1 gene, MTH1 gene, or MTH1 and STD1 genes of a yeast cell were deleted to verify effects of activity decrease of the genes caused by the gene deletion on yeast cell growth, glucose consumption, and ethanol production.

(1) Preparation of Strain in which STD1 Activity is Decreased

To delete STD1 gene, DNA corresponding to the gene was removed by a homologous recombination with a PCR cassette having loxP sites before and after a marker gene capable of synthesizing one of essential amino acids, and the marker gene was removed by a homologous recombination between the loxP sites by using a vector expressing cre recombinase. First, a pUG73 vector (Euroscarf, Acc. no. P30118) was used to prepare a PCR fragment by the following method. DNA of the pUG73 vector was used as a template, and primers of SEQ ID NOS: 22 and 23 were used to prepare an STD1 gene deletion cassette by preparing a Leu2 PCR fragment in which a promoter 3' sequence and a terminator 5' sequence of STD1 gene were overlapped before and after the fragment. The STD1 gene deletion cassette was introduced to S. cerevisiae (CEN.PK2-1D (MATα ura3-52; trp1-289; leu2-3,112; his3Δ, 1; MAL2-8C; SUC2) EUROSCARF accession number: 30000B: also referred to as "CEN.PK2-1D strain" hereinafter) by a general heat shock transformation method. After transformation, cells were cultured in a LEUCINE drop out plate medium Yeast nitrogen base without amino acids (Sigma-Aldrich: Cat. No. Y0626) 6.7 g/L, yeast synthetic drop-out without LEUCINE (Sigma-Aldrich) 1.9 g/L, agar (USB Products: CAS#9002-18-0) 15 g/L, and glucose 2 (w/v) %, hereinafter referred to as SC-Leu) to select only cells in which STD1 gene was substituted with LEU2 gene. The substitution in the strain was verified by performing a PCR by using the genome of the obtained cell as a template and by using primers of SEQ ID NO: 24 and SEQ ID NO: 25. After verification, a pSH62 (Euroscarf, Acc. no. P30120) vector was introduced to the selected cells by heat shock transformation. After transformation, cells were cultured in a HISTIDINE drop out medium (Yeast nitrogen base without amino acids (Sigma-Aldrich: Cat. No. Y0626) 6.7 g/L, yeast synthetic drop-out without HISTIDINE (Sigma-Aldrich) 1.9 g/L, agar (USB Products: CAS#9002-18-0) 15 g/L, and glucose 2 (w/v) %, hereinafter referred to as SC-His) to select only cells to which a pSH62 vector was inserted. The selected cells were cultured for 24 hours in a YP-GAL medium (Bacto Peptone (BD & Difco: Cat. No. 211677) 20 g/L, yeast extract (BD & Difco: Cat. No. 212750) 10 g/L, agar (USB Products: CAS. No. 9002-18-0) 15 g/L, and galactose (BD & Difco: Cat. No. 216310) 2 (w/v) %) to induce expression of cre recombinase by GAL promoter. After diluting the cell culture at a ratio of 1/1000, the cells were cultured for 24 hours in a YPD plate medium (Bacto Peptone (BD & Difco: Cat. No. 211677) 20 g/L, yeast extract (BD & Difco: Cat. No. 212750) 10 g/L, agar (USB Products: CAS#9002-18-0) 15 g/L, and glucose 2 (w/v) %). A colony was dispersed in a triple distilled water, and the resulting solution was spotted on YPD, SC-His, SC-Leu plate media to select only the cells in which both the LEU2 gene, which was substituted for STD1, and the pSH62 vector were deleted. Finally, the gene deletion was verified by performing a PCR by using the genome of the obtained cell as a template and by using primers of SEQ ID NO: 24 and SEQ ID NO: 26.

(2) Preparation of Strain in which MTH1 Activity is Decreased

To delete MTH1 gene, DNA corresponding to the gene was removed by homologous recombination with a gene capable of synthesizing an essential amino acid, and the gene was removed by using a cre plasmid. First, a pUG73 vector was used to prepare a PCR fragment by the following method. DNA of the pUG73 vector was used as a template, and primers of SEQ ID NOS: 27 and 28 were used to prepare an MTH1 gene deletion cassette by preparing a Leu2 PCR fragment in which a promoter 3' sequence and a terminator 5' sequence of MTH1 gene were overlapped before and after the fragment. The STD1 gene deletion cassette was introduced to S. cerevisiae CEN.PK2-1 D by a heat shock transformation method. After transformation, cells were cultured in SC-LEU medium to select only cells in which MTH1 gene was substituted with LEU2 gene. The substitution in the strain was verified by performing a PCR by using the genome of the obtained cell as a template and by using primers of SEQ ID NO: 29 and SEQ ID NO: 25. After verification, a pSH62 vector was introduced to the selected cells by heat shock transformation. After transformation, cells were cultured in an SC-His medium to select only cells to which a pSH62 vector was inserted. The selected cells were cultured for 24 hours in a YP-GAL medium to induce expression of cre recombinase by GAL promoter. After diluting the cell culture at a ratio of 1/1000, the cells were cultured for 24 hours in a YPD plate medium. A colony was dispersed in a triple distilled water, and the resulting solution was spotted on YPD, SC-His, SC-Leu plate media to select only the cells in which both the LEU2 gene, which was substituted for MTH1, and the pSH62 vector were deleted. Finally, the gene deletion was verified by performing a PCR by using the genome of the obtained cell as a template and by using primers of SEQ ID NO: 29 and SEQ ID NO: 30.

(3) Preparation of Strain in which STD1 and MTH1 Activity is Decreased

To delete both STD1 and MTH1 genes, the method described (2) was performed with a STD1 deleted strain to prepare a strain in which both STD1 and MTH1 genes were deleted.

(4) Verification of Growth, Glucose Consumption, and Ethanol Production of Transformed Yeast Cell The transformed yeast cell prepared above was first inoculated to a YPD medium including 4% glucose, and 16 hours later inoculated to a YPD medium including 8% glucose until an $OD_{600}$ became 5. Then, the resulting medium was stirred at 30° C. at 170 rpm to culture under aerobic conditions for 10 hours. Cell growth during the culturing was measured by measuring an $OD_{600}$ value by using a spectrophotometer. The residual glucose and ethanol concentrations were analyzed by high performance liquid chromatography (HPLC).

(5) Culturing Results

The culturing results including cell growth ($OD_{600}$ value), and residual glucose and ethanol concentrations in the medium after 10 hours of culturing are shown in Table 1.

TABLE 1

| Strain | Cell Growth ($OD_{600}$) | Glucose Consumption (g/L) | Ethanol Production (g/L) |
| --- | --- | --- | --- |
| Control Group | 24.8 | 74 | 32.8 |
| MTH1 gene deleted strain | 17.2 | 32 | 12.6 |
| STD1 gene deleted strain | 25.2 | 78 | 35.0 |
| MTH1 and STD1 genes deleted strain | 28.3 | 80 | 35.5 |

In table 1, the control group was cultured under the same conditions, except that a pRS416 vector was introduced to *S. cerevisiae* CEN.PK2-1D. The MTH1 gene deleted strain represents *S. cerevisiae* CEN.PK2-1D (Δ mth1), the STD1 gene deleted strain represents *S. cerevisiae* CEN.PK2-1D (Δ std1), and the MTH1 and STD1 genes deleted strain represents *S. cerevisiae* CEN.PK2-1D (Δ std1, Δ mth1).

As shown in Table 1, the cell growth, glucose consumption, and ethanol production of the STD1 gene deleted strain were higher than those of the control group by 1.6%, 5.4%, and 6.7%, respectively. The glucose consumption rate of the STD1 gene deleted strain was 7.1 g/L/h, which was about 10% higher than that of the control group, which was 6.5 g/L/h. The glucose consumption data represent the glucose consumption up to six hours.

In addition, the cell growth, glucose consumption, and ethanol production of the MTH1 and STD1 genes deleted strain were higher than those of the control group by 14.1%, 8.1%, and 8.2%, respectively. The glucose consumption rate of the MTH1 and STD1 genes deleted strain was 7.8 g/L/h, which was about 20% higher than that of the control group, which was 6.5 g/L/h. The glucose consumption data represent the glucose consumption up to six hours.

Example 2. Effect of Activity Decrease of STD1 Gene, MTH1 Gene, or MTH1 and STD1 Genes in Yeast Cell Having Improved Lactate Productivity In Example 2, MTH1 gene, STD1 gene, or MTH1 and STD1 genes of a yeast cell having improved lactate productivity were deleted to verify effects of activity decrease of the genes caused by the gene deletion on yeast cell growth, glucose consumption, and lactate production.

To improve lactate productivity in *S. cerevisiae* CEN.PK2-1D, a gene encoding an enzyme involved in a pathway from pyruvate to ethanol, which is a pathway that directs metabolites away from lactate production, was deleted, wherein the gene encodes pyruvate decarboxylase 1 (PDC1). PDC1 is an enzyme that catalyzes conversion of pyruvate to acetaldehyde and $CO_2$. At the same time the pdc1 gene was deleted, a lactate dehydrogenase (ldh) gene was introduced. LDH is an enzyme catalyzing a reaction of converting pyruvate to lactate.

In addition, a gene encoding L-lactate cytochrome-c oxidoreductase (cyb2) which catalyzes a reaction of converting lactate to pyruvate was deleted. At the same time the cyb2 gene was deleted, a lactate dehydrogenase (ldh) gene was introduced.

In addition, to strengthen the metabolic flow of pyruvate in glycolysis, a gene encoding glycerol-3-phosphate dehydrogenase 1 (gpd1) having the activity of catalyzing a reaction of converting dihydroxy acetone phosphate (DHAP) to glycerol-3-phosphate (G3P) was deleted. GPD1 converts NADH to $NAD^+$ simultaneously with the reaction. At the same time the gpd1 gene was deleted, a lactate dehydrogenase (ldh) gene was introduced.

(1) Preparation of *S. cerevisiae* CEN.PK2-1D (Δ Pdc1::Ldh)

(1.1) Preparation of Vector for Deleting Pdc1 and Introducing Ldh

To block a pathway from pyruvate to acetaldehyde and then to ethanol in *S. cerevisiae* CEN.PK2-1D, a gene encoding pyruvate decarboxylase1 (pdc1) was removed. To express an Ldh derived from *Pelodiscus sinensis japonicus*, at the same time the pdc1 gene was removed the pdc1 gene was substituted with a 'ldh cassette' to delete the pdc1 gene. Unless otherwise described, the term "cassette" refers to a unit sequence to which a promoter, an encoding sequence, and a terminator were operably linked to express a protein.

Specifically, to prepare a vector including the 'ldh cassette,' a CCW12 promoter sequence (SEQ ID NO: 20) and an 'ldh gene (SEQ ID NO: 15)' obtained by performing a PCR using a genomic DNA of *S. cerevisiae* as a template, and a primer pair of SEQ ID NOS: 31 and 32 as primers were digested by using SacI/XbaI and BamHI/SalI, respectively, and then linked to a pRS416 vector (ATCC87521) digested by using the same enzymes. The pRS416 vector is a yeast centromere shuttle plasmid having a T7 promoter, ampicillin resistance in bacteria, a URA3 cassette (selection marker) in yeast, and a restriction enzyme cloning site. Next, a 'HPH cassette' sequence (SEQ ID NO: 35), which was an amplification product obtained by performing a PCT using a pCEP4 plasmid (Invitrogen, Cat. no. V044-50) as a template and a primer pair of SEQ ID NOS: 33 and 34 as primers, was digested by using SacI and linked to the obtained vector digested by using the same enzyme to prepare a p416-ldh-HPH vector including the 'ldh cassette.' A pCEP4 plasmid is an episomal mammalian expression vector using a cytomegalovirus (CMV) immediate early enhance/promoter for a high level of transcription of a recombinant gene inserted to a multiple cloning site. pCEP4 has a hygromycin B resistance gene for stable selection in a transfected cell. The 'ldh cassette' refers to a region including an ldh gene and a regulatory region thereof to express the ldh gene. The ldh gene was transcribed under a CCW12 promoter. In addition, the 'HPH (hygromycin B phosphotransferase) cassette' refers to a region including a hygromycin B resistance gene and a regulatory region thereof to express a hygromycin B resistance gene.

To prepare a vector for deleting pdc1, an ldh gene fragment and a pUC57-Ura3HA vector (DNA2.0 Inc.; SEQ ID NO: 38) prepared by performing a PCR using p416-ldh-HPH as a template and a primer set of SEQ ID NOS: 36 and 37 as primers were respectively digested by using SacI and then linked to each other to prepare a pUC-uraHA-ldh vector. A cassette for deleting pdc1 was amplified from the vector by performing a PCR using sequences of SEQ ID NOS: 39 and 40 having a homologous sequence with the pdc1 gene. The SEQ ID NO: 39-1 to 39-41 and the SEQ ID NO: 40-1 to 40-44 represent the parts which were substituted with a pdc1 gene by a homologous recombination with a homologous sequence of *S. cerevisiae* chromosome.

(1.2) Preparation of *S. cerevisiae* CEN.PK2-1D (Δ Pdc1::Ldh)

The cassette for pdc1 deletion prepared in (1.1) was introduced to *S. cerevisiae* (CEN.PK2-1D, EUROSCARF accession number: 30000B). The cassette for pdc1 deletion was introduced by a general heat shock transformation. After the transformation, the cell was cultured in a uracil drop out medium to substitute the pdc1 ORF on the chromosome with the cassette.

To verify deletion of pdc1 in the cell obtained as a result, a PCR was performed by using the genome of the cell as a template and a primer set of SEQ ID NOS: 41 and 42 as primers to verify the deletion of pdc1 gene and introduction of ldh gene. As a result, *S. cerevisiae* CEN.PK2-1 D (Δ pdc1::ldh) was prepared.

(2) Preparation of *S. cerevisiae* CEN.PK2-1D (Δ Pdc1::Ldh, Δ Cyb2::Ldh)

(2.1) Preparation of Vector for Deleting Cyb2

To block a pathway from lactate to pyruvate in *S. cerevisiae* CEN.PK2-1 D (Δ pdc1::ldh) obtained in (1), cyb2 gene was removed.

Specifically, a cassette for cyb2 deletion was obtained by performing a PCR by using pUC-uraHA-ldh obtained in (1.1) as a template and cyb2 homologous sequences of SEQ ID NOS: 43 and 44 as primers. The SEQ ID NO: 43-1 to 43-45 and the SEQ ID NO: 44-1 to 44-45 represent the parts which were substituted with a cyb2 gene by a homologous recombination with *S. cerevisiae* chromosome.

(2.2) Preparation of *S. cerevisiae* CEN.PK2-1D (Δ Pdc1:: Ldh, Δ Cyb2::Ldh)

The cassette for cyb2 deletion prepared in (2.1) was introduced to *S. cerevisiae* CEN.PK2-1D (Δ pdc1::ldh). The cassette for cyb2 deletion was introduced by a general heat shock transformation. After the transformation, the cell was cultured in a uracil drop out medium to substitute the cyb2 ORF on the chromosome with the cassette.

To verify deletion of cyb2 in the cell obtained as a result, a PCR was performed by using the genome of the cell as a template and a primer set of SEQ ID NOS: 45 and 46 as primers to verify the deletion of cyb2 gene. As a result, *S. cerevisiae* CEN.PK2-1D (Δ pdc1::ldh, Δ cyb2::ldh) was prepared.

(3) Preparation of *S. cerevisiae* CEN.PK2-1D (Δ Pdc1:: Ldh, Δ Cyb2, a Gpd1::Ldh)

(3.1) Preparation of Vector for Gpd1 Deletion

To block a pathway from DHAP to G3P in *S. cerevisiae* CEN.PK2-1 D (Δ pdc1::ldh, Δ cyb2) prepared in (2), a gene encoding glycerol-3-phosphate dehydrogenase 1 (gpd1) was removed.

Specifically, a cassette for gpd1 deletion was obtained by performing a PCR by using pUC-uraHA-ldh obtained in (1.1) as a template and gpd1 homologous sequences of SEQ ID NOS: 47 and 48 as primers. The SEQ ID NO: 47-1 to 47-50 and the SEQ ID NO: 48-1 to 48-50 represent the parts which were substituted with a gpd1 gene by a homologous recombination with *S. cerevisiae* chromosome.

(3.2) Preparation of *S. cerevisiae* CEN.PK2-1D (Δ Pdc1:: Ldh, Δ Cyb2::Ldh, Δ Gpd1::Ldh)

The cassette for gpd1 deletion prepared in (3.1) was introduced to *S. cerevisiae* CEN.PK2-1D (Δ pdc1::ldh, Δ cyb2::ldh) prepared in (2). The cassette for gpd1 deletion was introduced by a general heat shock transformation. After the transformation, the cell was cultured in a uracil drop out medium to substitute the gpd1 ORF on the chromosome with the cassette.

To verify deletion of gpd1 in the cell obtained as a result, a PCR was performed by using the genome of the cell as a template and a primer set of SEQ ID NOS: 49 and 50 as primers to verify the deletion of gpd1 gene. As a result, *S. cerevisiae* CEN.PK2-1D (Δ pdc1::ldh, Δ cyb2::ldh, Δ gpd1:: ldh) was prepared.

*S. cerevisiae* CEN.PK2-1D (Δ pdc1::ldh, Δ cyb2::ldh, Δ gpd1::ldh) was internationally deposited on May 30, 2013 with Accession Number KCTC12415BP to Korean Collection for Type Cultures (KCTC) which is an International Depositary Authority according to Budapest Treaty.

2. Verification of Lactate Production of Transformed Yeast Cell

The transformed yeast cell prepared above was inoculated to 50 ml of a minimal Ura drop-out media including 5% glucose until an OD$_{600}$ became 1. Then, the resulting medium was stirred at 30° C. at 90 rpm to culture under microaerobic conditions for 48 hours. The residual lactate concentration was analyzed by high performance liquid chromatography (HPLC).

3. Culturing Results

The culturing results, which are lactate concentrations in the medium, are shown in Table 2.

TABLE 2

| Strain | Lactate Production (g/L) | Lactate Yield (%) |
|---|---|---|
| Control Group | 10.8 | 13.5 |
| MTH1 gene deleted strain | 10.4 | 13.1 |
| STD1 gene deleted strain | 13.4 | 16.8 |
| STD1 and MTH1 genes deleted strain | 12.6 | 15.8 |

In Table 2, the control group represents *S. cerevisiae* CEN.PK2-1D (Δ pdc1::ldh, Δ cyb2::ldh, Δ gpd1::ldh), the MTH1 gene deleted strain represents *S. cerevisiae* CEN.PK2-1D (Δ pdc1::ldh, Δ cyb2::ldh, Δ gpd1::ldh, Δ mth1), the STD1 gene deleted strain represents *S. cerevisiae* CEN.PK2-1 D (Δ pdc1::ldh, Δ cyb2::ldh, Δ gpd1::ldh, Δ std1), and the MTH1 and STD1 genes deleted strain represents *S. cerevisiae* CEN.PK2-1D (Δ pdc1::ldh, Δ cyb2::ldh, Δ gpd1::ldh, Δ std1, Δ mth1).

As shown in Table 1, the lactate productivity of the STD1 gene deleted strain was 13.4 g/L, which was higher than that of the control group, which was 10.8 g/L. The lactate yield of the STD1 gene deleted strain was also higher 16.8% which was higher than that of the control group, which was 13.5%. Therefore, the lactate productivity of the STD1 gene deleted strain was improved by about 24% in comparison with the control group. In addition, the lactate productivity of the STD1 and MTH1 genes deleted strain was 12.6 g/L, which was higher than that of the control group, which was 10.8 g/L. The lactate yield of the STD1 gene deleted strain was 15.8% which was higher than that of the control group at 13.5%. Therefore, the lactate productivity of the STD1 gene deleted strain was improved by about 17% in comparison with the control group.

As described above, a yeast cell according to one aspect of an exemplary embodiment may consume glucose at an increased speed.

A method of producing pyruvate or a pyruvate-derived product according to one aspect of an exemplary embodiment may be used to efficiently produce pyruvate or a pyruvate-derived product.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A genetically modified yeast cell comprising:
   a deletion or disruption mutation of a gene encoding STD1 wherein the genetically modified yeast cell has decreased STD1 activity in comparison with a parent cell that does not have a deletion or disruption mutation of a gene encoding STD1,
   a deletion or disruption mutation of a gene encoding MTH1 wherein the genetically modified yeast has decreased MTH1 activity in comparison with a parent cell that does not have a deletion or disruption mutation of a gene encoding MTH1, and
   increased activity of an enzyme of a pathway for synthesizing a pyruvate-derived material from pyruvate,
   wherein the genetically modified yeast cell consumes glucose at an increased rate in comparison with a parent cell, and produces one or more glycolysis intermediates at an increased rate in comparison with a parent cell.

2. The genetically modified yeast cell of claim 1, wherein the glycolysis intermediates comprise dihydroxyacetone phosphate (DHAP), glyceraldehyde 3-phosphate (GAP), pyruvate, or a combination thereof.

3. The genetically modified yeast cell of claim 1, wherein the genetically modified yeast cell produces a glycolysis intermediates-derived material at an increased rate compared to a parent cell, and the glycolysis intermediates-derived material comprises glyceol-3-phosphate (G3P), glycerol, acetyl-CoA, ethanol, acetic acid, lactate, a TCA cycle intermediate, or a combination thereof.

4. The genetically modified yeast cell of claim 3, wherein genetically modified yeast cell produces a TCA cycle intermediate at an increased rate compared to a parent cell, and the TCA cycle intermediate is citric acid, itaconic acid, isocitric acid, oxalosuccinic acid, a-ketoglutaric acid, succinic acid, succinyl-CoA, fumaric acid, maleic acid, oxaloacetic acid, or a combination thereof, and the TCA cycle intermediate-derived material is 1,3-butanediol (1,3-BDO), 1,4-butanediol (1,4-BDO), butanol, or isobutanol.

5. The genetically modified yeast cell of claim 3, wherein the genetically modified yeast cell has increased activity of an enzyme of a pathway for synthesizing glycerol from DHAP, compared to a parent cell.

6. The genetically modified yeast cell of claim 3, wherein the expression of a polynucleotide encoding the enzyme of a pathway for synthesizing a pyruvate-derived material from pyruvate is increased in the genetically modified yeast cell, and the expression of a polynucleotide encoding an enzyme of a pathway for synthesizing glycerol from DHAP is increased in the genetically modified yeast cell.

7. The genetically modified yeast cell of claim 1, wherein the genetically modified yeast cell is a strain belonging to *Saccharomyces, Zygosaccharomyces, Pichia, Kluyveromyces, Candida, Shizosaccharomyces, Issachenkia,* or *Hansenula*.

8. The genetically modified yeast cell of claim 1, wherein the genetically modified yeast cell has increased activity of an enzyme that converts pyruvate to lactate or an enzyme of a pathway for converting pyruvate to ethanol compared to a parent cell.

9. The genetically modified yeast cell of claim 1, wherein the yeast cell has a higher level of lactate production or a higher level of ethanol production compared to that of a parent cell.

10. The genetically modified yeast cell of claim 9, wherein enzyme that converts pyruvate to lactate is classified as EC 1.1.1.27, EC 1.1.1.28, and the enzyme of a pathway for converting pyruvate to ethanol is pyruvate decarboxylase classified as EC 4.1.1.1 or alcohol dehydrogenase (ADH) classified as EC 1.1.1.2.

11. The genetically modified yeast cell of claim 1, wherein the genetically modified yeast cell further comprises increased expression of an enzyme classified as EC 1.1.1.27, EC 1.1.1.28, or a combination thereof.

12. The genetically modified yeast cell of claim 1 comprising an exogenous gene encoding an enzyme of a pathway for synthesizing a pyruvate-derived material from pyruvate.

13. A method of producing a glycolysis intermediate, wherein the method comprises culturing the genetically modified yeast cell of claim 1 in a cell culture medium, whereby the genetically modified yeast cell produces a glycolysis intermediate; and recovering the glycolysis intermediate from a culture solution.

* * * * *

```
                              SEQUENCE LISTING

<160> NUMBER OF SEQ ID NOS: 50

<210> SEQ ID NO 1
<211> LENGTH: 444
<212> TYPE: PRT
<213> ORGANISM: Saccharomyces cerevisiae

<400> SEQUENCE: 1

Met Phe Val Ser Pro Pro Ala Thr Ala Arg Asn Gln Val Leu Gly
 1               5                  10                  15

Lys Arg Lys Ser Lys Arg His Asp Glu Asn Pro Lys Asn Val Gln Pro
                 20                  25                  30

Asn Ala Asp Thr Glu Met Thr Asn Ser Val Pro Ser Ile Gly Phe Asn
             35                  40                  45

Ser Asn Leu Pro His Asn Asn Gln Glu Ile Asn Thr Pro Asn His Tyr
         50                  55                  60

Asn Leu Ser Ser Asn Ser Gly Asn Val Arg Ser Asn Asn Asn Phe Val
 65                  70                  75                  80

Thr Thr Pro Pro Glu Tyr Ala Asp Arg Ala Arg Ile Glu Ile Ile Lys
                 85                  90                  95

Arg Leu Leu Pro Thr Ala Gly Thr Lys Pro Met Glu Val Asn Ser Asn
                100                 105                 110

Thr Ala Glu Asn Ala Asn Ile Gln His Ile Asn Thr Pro Asp Ser Gln
            115                 120                 125

Ser Phe Val Ser Asp His Ser Ser Ser Tyr Glu Ser Ser Ile Phe Ser
        130                 135                 140

Gln Pro Ser Thr Ala Leu Thr Asp Ile Thr Thr Gly Ser Ser Leu Ile
145                 150                 155                 160

Asp Thr Lys Thr Pro Lys Phe Val Thr Glu Val Thr Leu Glu Asp Ala
                165                 170                 175

Leu Pro Lys Thr Phe Tyr Asp Met Tyr Ser Pro Glu Val Leu Met Ser
                180                 185                 190

Asp Pro Ala Asn Ile Leu Tyr Asn Gly Arg Pro Lys Phe Thr Lys Arg
            195                 200                 205

Glu Leu Leu Asp Trp Asp Leu Asn Asp Ile Arg Ser Leu Leu Ile Val
        210                 215                 220

Glu Gln Leu Arg Pro Glu Trp Gly Ser Gln Leu Pro Thr Val Val Thr
225                 230                 235                 240

Ser Gly Ile Asn Leu Pro Gln Phe Arg Leu Gln Leu Leu Pro Leu Ser
```

```
                    245                 250                 255
Ser Ser Asp Glu Phe Ile Ile Ala Thr Leu Val Asn Ser Asp Leu Tyr
                260                 265                 270

Ile Glu Ala Asn Leu Asp Arg Asn Phe Lys Leu Thr Ser Ala Lys Tyr
            275                 280                 285

Thr Val Ala Ser Ala Arg Lys Arg His Glu Glu Met Thr Gly Ser Lys
        290                 295                 300

Glu Pro Ile Met Arg Leu Ser Lys Pro Glu Trp Arg Asn Ile Ile Glu
305                 310                 315                 320

Asn Tyr Leu Leu Asn Val Ala Val Glu Ala Gln Cys Arg Tyr Asp Phe
                325                 330                 335

Lys Gln Lys Arg Ser Glu Tyr Lys Arg Trp Lys Leu Leu Asn Ser Asn
            340                 345                 350

Leu Lys Arg Pro Asp Met Pro Pro Ser Leu Ile Pro His Gly Phe
        355                 360                 365

Lys Ile His Asp Cys Thr Asn Ser Gly Ser Leu Leu Lys Lys Ala Leu
        370                 375                 380

Met Lys Asn Leu Gln Leu Lys Asn Tyr Lys Asn Asp Ala Lys Thr Leu
385                 390                 395                 400

Gly Ala Gly Thr Gln Lys Asn Val Val Asn Lys Val Ser Leu Thr Ser
                405                 410                 415

Glu Glu Arg Ala Ala Ile Trp Phe Gln Cys Gln Thr Val Tyr Gln
            420                 425                 430

Arg Leu Gly Leu Asp Trp Lys Pro Asp Gly Met Ser
        435                 440

<210> SEQ ID NO 2
<211> LENGTH: 1335
<212> TYPE: DNA
<213> ORGANISM: Saccharomyces cerevisiae

<400> SEQUENCE: 2
atgtttgttt caccacctcc agcaacagcg aggaaccaag tattagggaa agaaaatcg       60 aaaagacatg acgaaaatcc aaagaatgtt caacccaacg ctgacacaga atgacaaat     120 agcgttcctt ctattggatt caacagcaat cttccacata taaccaaga ataaacaca     180 ccaaatcact ataatttgag ttccaattca ggaaatgtta ggagcaacaa caattttgtt     240
actacaccac cagaatatgc agacagggca agaatagaaa tcataaaaag gttattgcct     300
actgcaggaa ctaaacctat ggaagtgaac agtaatactg cagaaaatgc aaatatccaa     360
cacataaata ccccggacag tcaaagtttt gtttcagacc attcatcttc atacgaatcg     420
agtatatttt cacagccatc tactgctctt acggacatca ccacaggcag ctcgttaatt     480
gatacaaaaa cacctaagtt cgtcacagaa gtaacacttg aagacgcttt acccaaaaca     540
ttctatgata tgtattctcc cgaagttctg atgtctgatc cagcaaatat actttataac     600
ggacgtccta agtttacaaa gcgcgaattg ctggactggg atctaaacga tatacgatcc     660
ttgttaattg tggaacaatt aaggccagaa tggggttccc agttaccgac ggtagtgacc     720
tccggtataa acttaccgca attcagacta caattacttc ccctaagttc cagtgatgag     780
tttataatag cgacattggt taactcagac ttatacatag aagcaaatct agaccgcaat     840
tttaagttga caagcgcaaa atatacagtt gcatcagcaa gaaaagaca tgaagaaatg     900 actgggtcaa aggaacccat tatgcgtcta tcaaagcctg aatggagaaa tataattgag     960
aactatttat taaatgttgc cgtcgaggcc caatgcagat atgactttaa acaaaagcgc    1020
```

```
tccgaataca agagatggaa attactaaat tcaaatttga aaaggcctga catgccgcct    1080
ccaagcctca taccgcatgg ttttaaaata catgactgca ctaactctgg tagtctttta    1140
aaaaaggctt taatgaaaaa tttgcaacta aaaattata aaaatgatgc taagacatta    1200
ggtgctggta cacagaaaaa tgtcgttaat aaggtttctc taacttcaga ggagagggct    1260
gccatctggt ttcaatgcca aacacaggtt tatcaaaggt tggggttaga ttggaagcct    1320
gatggaatgt cctag                                                    1335
```

<210> SEQ ID NO 3
<211> LENGTH: 433
<212> TYPE: PRT
<213> ORGANISM: Saccharomyces cerevisiae

<400> SEQUENCE: 3

```
Met Phe Val Ser Pro Pro Ala Thr Ser Lys Asn Gln Val Leu Gln
  1               5                  10                  15

Arg Arg Pro Leu Glu Ser Thr Asn Ser Asn His Gly Phe Ala Ser Ser
             20                  25                  30

Leu Gln Ala Ile Pro Glu Asn Thr Met Ser Gly Ser Asp Asn Ala Ser
         35                  40                  45

Phe Gln Ser Leu Pro Leu Ser Met Ser Ser Ser Gln Ser Thr Thr Ser
     50                  55                  60

Ser Arg Arg Glu Asn Phe Val Asn Ala Pro Pro Glu Tyr Thr Asp Arg
 65                  70                  75                  80

Ala Arg Asp Glu Ile Lys Lys Arg Leu Leu Ala Ser Ser Pro Ser Arg
                 85                  90                  95

Arg Ser His His Ser Ser Ser Met His Ser Ala Ser Arg Arg Ser Ser
            100                 105                 110

Val Ala Glu Ser Gly Ser Leu Leu Ser Asp Asn Ala Ser Ser Tyr Gln
        115                 120                 125

Ser Ser Ile Phe Ser Ala Pro Ser Thr Val His Thr Gln Leu Thr Asn
    130                 135                 140

Asp Ser Ser Phe Ser Glu Phe Pro Asn His Lys Leu Ile Thr Arg Val
145                 150                 155                 160

Ser Leu Asp Glu Ala Leu Pro Lys Thr Phe Tyr Asp Met Tyr Ser Pro
                165                 170                 175

Asp Ile Leu Leu Ala Asp Pro Ser Asn Ile Leu Cys Asn Gly Arg Pro
            180                 185                 190

Lys Phe Thr Lys Arg Glu Leu Leu Asp Trp Asp Leu Asn Asp Ile Arg
        195                 200                 205

Ser Leu Leu Ile Val Glu Lys Leu Arg Pro Glu Trp Gly Asn Gln Leu
    210                 215                 220

Pro Glu Val Ile Thr Val Gly Asp Asn Met Pro Gln Phe Arg Leu Gln
225                 230                 235                 240

Leu Leu Pro Leu Tyr Ser Ser Asp Glu Thr Ile Ile Ala Thr Leu Val
                245                 250                 255

His Ser Asp Leu Tyr Met Glu Ala Asn Leu Asp Tyr Glu Phe Lys Leu
            260                 265                 270

Thr Ser Ala Lys Tyr Thr Val Ala Thr Ala Arg Lys Arg His Glu His
        275                 280                 285

Ile Thr Gly Arg Asn Glu Ala Val Met Asn Leu Ser Lys Pro Glu Trp
    290                 295                 300

Arg Asn Ile Ile Glu Asn Tyr Leu Leu Asn Ile Ala Val Glu Ala Gln
```

```
                305                 310                 315                 320
Cys Arg Phe Asp Phe Lys Gln Arg Cys Ser Glu Tyr Lys Lys Trp Lys
                    325                 330                 335

Leu Gln Gln Ser Asn Leu Lys Arg Pro Asp Met Pro Pro Ser Ile
                340                 345                 350

Ile Pro Arg Lys Asn Ser Thr Glu Thr Lys Ser Leu Leu Lys Lys Ala
                    355                 360                 365

Leu Leu Lys Asn Ile Gln Leu Lys Asn Pro Asn Asn Leu Asp Glu
                370                 375                 380

Leu Met Met Arg Ser Ser Ala Ala Thr Asn Gln Gln Gly Lys Asn Lys
385                 390                 395                 400

Val Ser Leu Ser Lys Glu Glu Lys Ala Thr Ile Trp Ser Gln Cys Gln
                    405                 410                 415

Ala Gln Val Tyr Gln Arg Leu Gly Leu Asp Trp Gln Pro Asp Ser Val
                420                 425                 430

Ser

<210> SEQ ID NO 4
<211> LENGTH: 1302
<212> TYPE: DNA
<213> ORGANISM: Saccharomyces cerevisiae

<400> SEQUENCE: 4
atgtttgttt caccaccacc agcaacttcg aaaaaccaag ttttacaacg acgtccatta      60
gaatcgacta acagtaatca tgggtttgca agctccctac aggccattcc ggaaaacacg     120
atgagtggca gtgataatgc ttctttcaa gtttgccac tatcaatgag tagctctcaa      180
tccacgactt cttcgagaag agagaacttt gtgaatgctc ctccggagta cactgataga     240
gctagagatg agattaaaaa aagattattg gcctcctcac ctagcagaag gtcacatcat     300
tcaagcagta tgcattcagc gagcaggaga tcaagcgtgg ctgaaagtgg gagtttactt     360
tcggataatg cctcgtctta tcaatcaagt atattttctg ccccctctac tgtgcacacg     420
caactaacta tgactcttc gttctccgaa tttcctaacc acaagttaat cacgagagtg     480
agcctggatg aagcattacc caaaacgttt tatgacatgt attcgccaga tattctatta     540
gcagacccat ccaacattct ctgtaacggg cgtcccaagt ttaccaagag agagttattg     600
gattgggatt taaacgatat aagatcgtta ttgatagtcg agaagttaag gcccgaatgg     660
ggtaatcaac taccggaagt aataacggtg ggtgataata tgccccagtt taggttacaa     720
ttattaccac tatattctag cgatgagacc ataatcgcaa cgttagtcca ttcggatctg     780
tacatggagg ctaacttaga ttatgaattc aaactaacca gcgccaaata tacagtagcg     840
accgctagaa aaagacatga gcatataact ggtagaaatg aagccgtcat gaatttgtcg     900
aaaccggaat ggagaaatat catcgaaaat tacctcttaa atatagcagt agaggcacaa     960
tgcaggtttg atttcaaaca agatgctcc gaatataaga atggaagtt acaacagtcc     1020 aacttaaaaa gaccggacat gcccccacca agcataatac cgcggaaaaa cagcacagaa    1080
acaaaatcgc ttctgaaaaa ggctttattg aagaacattc agttgaaaaa ccccaataat    1140
aaccttgatg aattgatgat gagatcaagc gccgcaacaa atcaacaggg aaaaaacaaa    1200
gtcagcttat ctaaagaaga aaaggctacg atatggtcgc aatgtcaggc acaagtttac   1260
caaagattag gattggattg gcagccggat tcagtatcct ga                        1302

<210> SEQ ID NO 5
```

```
<211> LENGTH: 563
<212> TYPE: PRT
<213> ORGANISM: Saccharomyces cerevisiae

<400> SEQUENCE: 5
```

| | | | | | | | | | | | | | | |
|---|---|---|---|---|---|---|---|---|---|---|---|---|---|---|
| Met | Ser | Glu | Ile | Thr | Leu | Gly | Lys | Tyr | Leu | Phe | Glu | Arg | Leu | Lys | Gln |
| 1 | | | | 5 | | | | | 10 | | | | | 15 |

Val Asn Val Asn Thr Val Phe Gly Leu Pro Gly Asp Phe Asn Leu Ser
                 20                  25                  30

Leu Leu Asp Lys Ile Tyr Glu Val Glu Gly Met Arg Trp Ala Gly Asn
             35                  40                  45

Ala Asn Glu Leu Asn Ala Ala Tyr Ala Ala Asp Gly Tyr Ala Arg Ile
 50                  55                  60

Lys Gly Met Ser Cys Ile Ile Thr Thr Phe Gly Val Gly Glu Leu Ser
65                   70                  75                   80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe

-continued

```
           385                 390                 395                 400
    Pro Asn Asn Thr Tyr Gly Ile Ser Gln Val Leu Trp Gly Ser Ile Gly
                        405                 410                 415

Phe Thr Thr Gly Ala Thr Leu Gly Ala Ala Phe Ala Ala Glu Glu Ile
                        420                 425                 430

Asp Pro Lys Lys Arg Val Ile Leu Phe Ile Gly Asp Gly Ser Leu Gln
                        435                 440                 445

Leu Thr Val Gln Glu Ile Ser Thr Met Ile Arg Trp Gly Leu Lys Pro
                        450                 455                 460

Tyr Leu Phe Val Leu Asn Asn Asp Gly Tyr Thr Ile Glu Lys Leu Ile
    465                 470                 475                 480

His Gly Pro Lys Ala Gln Tyr Asn Glu Ile Gln Gly Trp Asp His Leu
                        485                 490                 495

Ser Leu Leu Pro Thr Phe Gly Ala Lys Asp Tyr Glu Thr His Arg Val
                        500                 505                 510

Ala Thr Thr Gly Glu Trp Asp Lys Leu Thr Gln Asp Lys Ser Phe Asn
                        515                 520                 525

Asp Asn Ser Lys Ile Arg Met Ile Glu Ile Met Leu Pro Val Phe Asp
                        530                 535                 540

Ala Pro Gln Asn Leu Val Glu Gln Ala Lys Leu Thr Ala Ala Thr Asn
    545                 550                 555                 560

Ala Lys Gln

<210> SEQ ID NO 6
<211> LENGTH: 591
<212> TYPE: PRT
<213> ORGANISM: Saccharomyces cerevisiae

<400> SEQUENCE: 6

Met Leu Lys Tyr Lys Pro Leu Leu Lys Ile Ser Lys Asn Cys Glu Ala
    1               5                   10                  15

Ala Ile Leu Arg Ala Ser Lys Thr Arg Leu Asn Thr Ile Arg Ala Tyr
                    20                  25                  30

Gly Ser Thr Val Pro Lys Ser Lys Ser Phe Glu Gln Asp Ser Arg Lys
                35                  40                  45

Arg Thr Gln Ser Trp Thr Ala Leu Arg Val Gly Ala Ile Leu Ala Ala
            50                  55                  60

Thr Ser Ser Val Ala Tyr Leu Asn Trp His Asn Gly Gln Ile Asp Asn
    65                  70                  75                  80

Glu Pro Lys Leu Asp Met Asn Lys Gln Lys Ile Ser Pro Ala Glu Val
                    85                  90                  95

Ala Lys His Asn Lys Pro Asp Asp Cys Trp Val Val Ile Asn Gly Tyr
                    100                 105                 110

Val Tyr Asp Leu Thr Arg Phe Leu Pro Asn His Pro Gly Gly Gln Asp
                115                 120                 125

Val Ile Lys Phe Asn Ala Gly Lys Asp Val Thr Ala Ile Phe Glu Pro
            130                 135                 140

Leu His Ala Pro Asn Val Ile Asp Lys Tyr Ile Ala Pro Glu Lys Lys
    145                 150                 155                 160

Leu Gly Pro Leu Gln Gly Ser Met Pro Pro Glu Leu Val Cys Pro Pro
                    165                 170                 175

Tyr Ala Pro Gly Glu Thr Lys Glu Asp Ile Ala Arg Lys Glu Gln Leu
                    180                 185                 190

Lys Ser Leu Leu Pro Pro Leu Asp Asn Ile Ile Asn Leu Tyr Asp Phe
```

```
            195                 200                 205
Glu Tyr Leu Ala Ser Gln Thr Leu Thr Lys Gln Ala Trp Ala Tyr Tyr
210                 215                 220

Ser Ser Gly Ala Asn Asp Glu Val Thr His Arg Glu Asn His Asn Ala
225                 230                 235                 240

Tyr His Arg Ile Phe Phe Lys Pro Lys Ile Leu Val Asp Val Arg Lys
            245                 250                 255

Val Asp Ile Ser Thr Asp Met Leu Gly Ser His Val Asp Val Pro Phe
            260                 265                 270

Tyr Val Ser Ala Thr Ala Leu Cys Lys Leu Gly Asn Pro Leu Glu Gly
            275                 280                 285

Glu Lys Asp Val Ala Arg Gly Cys Gly Gln Gly Val Thr Lys Val Pro
            290                 295                 300

Gln Met Ile Ser Thr Leu Ala Ser Cys Ser Pro Glu Glu Ile Ile Glu
305                 310                 315                 320

Ala Ala Pro Ser Asp Lys Gln Ile Gln Trp Tyr Gln Leu Tyr Val Asn
            325                 330                 335

Ser Asp Arg Lys Ile Thr Asp Asp Leu Val Lys Asn Val Glu Lys Leu
            340                 345                 350

Gly Val Lys Ala Leu Phe Val Thr Val Asp Ala Pro Ser Leu Gly Gln
            355                 360                 365

Arg Glu Lys Asp Met Lys Leu Lys Phe Ser Asn Thr Lys Ala Gly Pro
370                 375                 380

Lys Ala Met Lys Lys Thr Asn Val Glu Glu Ser Gln Gly Ala Ser Arg
385                 390                 395                 400

Ala Leu Ser Lys Phe Ile Asp Pro Ser Leu Thr Trp Lys Asp Ile Glu
            405                 410                 415

Glu Leu Lys Lys Thr Lys Leu Pro Ile Val Ile Lys Gly Val Gln
            420                 425                 430

Arg Thr Glu Asp Val Ile Lys Ala Ala Glu Ile Gly Val Ser Gly Val
            435                 440                 445

Val Leu Ser Asn His Gly Gly Arg Gln Leu Asp Phe Ser Arg Ala Pro
450                 455                 460

Ile Glu Val Leu Ala Glu Thr Met Pro Ile Leu Glu Gln Arg Asn Leu
465                 470                 475                 480

Lys Asp Lys Leu Glu Val Phe Val Asp Gly Gly Val Arg Arg Gly Thr
            485                 490                 495

Asp Val Leu Lys Ala Leu Cys Leu Gly Ala Lys Gly Val Gly Leu Gly
            500                 505                 510

Arg Pro Phe Leu Tyr Ala Asn Ser Cys Tyr Gly Arg Asn Gly Val Glu
            515                 520                 525

Lys Ala Ile Glu Ile Leu Arg Asp Glu Ile Glu Met Ser Met Arg Leu
            530                 535                 540

Leu Gly Val Thr Ser Ile Ala Glu Leu Lys Pro Asp Leu Leu Asp Leu
545                 550                 555                 560

Ser Thr Leu Lys Ala Arg Thr Val Gly Val Pro Asn Asp Val Leu Tyr
            565                 570                 575

Asn Glu Val Tyr Glu Gly Pro Thr Leu Thr Glu Phe Glu Asp Ala
            580                 585                 590

<210> SEQ ID NO 7
<211> LENGTH: 391
<212> TYPE: PRT
<213> ORGANISM: Saccharomyces cerevisiae
```

<400> SEQUENCE: 7

Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
                35                  40                  45

Ile Ala Lys Val Val Ala Glu Asn Cys Lys Gly Tyr Pro Glu Val Phe
        50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
            115                 120                 125

Phe Leu Pro Arg Ile Cys Ser Gln Leu Lys Gly His Val Asp Ser His
130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
            195                 200                 205

Glu Gly Lys Asp Val Asp His Lys Val Leu Lys Ala Leu Phe His Arg
210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
            245                 250                 255

Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
            275                 280                 285

Glu Glu Thr Tyr Tyr Gln Glu Ser Ala Gly Val Ala Asp Leu Ile Thr
290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
            355                 360                 365

Ile Val Tyr Asn Asn Tyr Pro Met Lys Asn Leu Pro Asp Met Ile Glu
            370                 375                 380

Glu Leu Asp Leu His Glu Asp
385                 390

```
<210> SEQ ID NO 8
<211> LENGTH: 1692
<212> TYPE: DNA
<213> ORGANISM: Saccharomyces cerevisiae

<400> SEQUENCE: 8
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact gaacgtccc agctaagttg      540 ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720 ccagcttttcg tcaccccaat gggtaagggt tccattgacg aacaaccc aagatacggt      780 ggtgtttacg tcggtacctt gtccaagcca gaagttaagg aagccgttga atctgctgac     840 ttgatttttgt ctgtcggtgc tttgttgtct gatttcaaca ccggttcttt ctcttactct     900
tacaagacca agaacattgt cgaattccac tccgaccaca tgaagatcag aaacgccact     960
ttcccaggtg tccaaatgaa attcgttttg caaaagttgt tgaccactat tgctgacgcc    1020
gctaagggtt acaagccagt tgctgtccca gctagaactc cagctaacgc tgctgtccca    1080
gcttctaccc cattgaagca agaatggatg tggaaccaat tgggtaactt cttgcaagaa    1140
ggtgatgttg tcattgctga aaccggtacc tccgctttcg gtatcaacca aaccactttc    1200
ccaaacaaca cctacggtat ctctcaagtc ttatggggt ccattggttt caccactggt     1260
gctaccttgg gtgctgcttt cgctgctgaa gaaattgatc aaagaagag agttatctta     1320 ttcattggtg acggttcttt gcaattgact gttcaagaaa tctccaccat gatcagatgg     1380
ggcttgaagc catacttgtt cgtcttgaac aacgatggtc acaccattga aaagttgatt    1440
cacggtccaa aggctcaata caacgaaatt caaggttggg accacctatc cttgttgcca    1500
actttcggtg ctaaggacta tgaaacccac agagtcgcta ccaccggtga atgggacaag    1560
ttgacccaag acaagtcttt caacgacaac tctaagatca gaatgattga aatcatgttg    1620
ccagtcttcg atgctccaca aaacttggtt gaacaagcta agttgactgc tgctaccaac    1680
gctaagcaat aa                                                        1692

<210> SEQ ID NO 9
<211> LENGTH: 1776
<212> TYPE: DNA
<213> ORGANISM: Saccharomyces cerevisiae

<400> SEQUENCE: 9
atgctaaaat acaaaccttt actaaaaatc tcgaagaact gtgaggctgc tatcctcaga      60
gcgtctaaga ctagattgaa cacaatccgc gcgtacggtt ctaccgttcc aaaatccaag     120
tcgttcgaac aagactcaag aaaacgcaca cagtcatgga ctgccttgag agtcggtgca     180
```

| | |
|---|---|
| attctagccg ctactagttc cgtggcgtat ctaaactggc ataatggcca aatagacaac | 240 |
| gagccgaaac tggatatgaa taaacaaaag atttcgcccg ctgaagttgc caagcataac | 300 |
| aagcccgatg attgttgggt tgtgatcaat ggttacgtat acgacttaac gcgattccta | 360 |
| ccaaatcatc caggtgggca ggatgttatc aagtttaacg ccgggaaaga tgtcactgct | 420 |
| atttttgaac cactacatgc tcctaatgtc atcgataagt atatagctcc cgagaaaaaa | 480 |
| ttgggtcccc ttcaaggatc catgcctcct gaacttgtct gtcctcctta tgctcctggt | 540 |
| gaaactaagg aagatatcgc tagaaaagaa caactaaaat cgctgctacc tcctctagat | 600 |
| aatattatta acctttacga cttttgaatac ttggcctctc aaactttgac taaacaagcg | 660 |
| tgggcctact attcctccgg tgctaacgac gaagttactc acagagaaaa ccataatgct | 720 |
| tatcatagga ttttttttcaa accaaagatc cttgtagatg tacgcaaagt agacatttca | 780 |
| actgacatgt tgggttctca tgtggatgtt cccttctacg tgtctgctac agctttgtgt | 840 |
| aaactgggaa accccttaga aggtgaaaaa gatgtcgcca gaggttgtgg ccaaggtgtg | 900 |
| acaaaagtcc cacaaatgat atctactttg gcttcatgtt cccctgagga aattattgaa | 960 |
| gcagcaccct ctgataaaca aattcaatgg taccaactat atgttaactc tgatagaaag | 1020 |
| atcactgatg atttggttaa aaatgtagaa aagctgggtg taaaggcatt atttgtcact | 1080 |
| gtggatgctc caagtttagg tcaaagagaa aaagatatga agctgaaatt ttccaataca | 1140 |
| aaggctggtc aaaagcgat gaagaaaact aatgtagaag aatctcaagg tgcttcgaga | 1200 |
| gcgttatcaa agtttattga cccctctttg acttggaaag atatagaaga gttgaagaaa | 1260 |
| aagacaaaac tacctattgt tatcaaaggt gttcaacgta ccgaagatgt tatcaaagca | 1320 |
| gcagaaatcg gtgtaagtgg ggtggttcta tccaatcatg gtggtagaca attagatttt | 1380 |
| tcaagggctc ccattgaagt cctggctgaa accatgccaa tcctggaaca acgtaacttg | 1440 |
| aaggataagt tggaagtttt cgtggacggt ggtgttcgtc gtggtacaga tgtcttgaaa | 1500 |
| gcgttatgtc taggtgctaa aggtgttggt ttgggtagac cattcttgta tgcgaactca | 1560 |
| tgctatggtc gtaatggtgt tgaaaaagcc attgaaattt taagagatga aattgaaatg | 1620 |
| tctatgagac tattaggtgt tactagcatt gcggaattga agcctgatct tttagatcta | 1680 |
| tcaacactaa aggcaagaac agttggagta ccaaacgacg tgctgtataa tgaagtttat | 1740 |
| gagggaccta ctttaacaga atttgaggat gcatga | 1776 |

<210> SEQ ID NO 10
<211> LENGTH: 1176
<212> TYPE: DNA
<213> ORGANISM: Saccharomyces cerevisiae

<400> SEQUENCE: 10

| | |
|---|---|
| atgtctgctg ctgctgatag attaaactta acttccggcc acttgaatgc tggtagaaag | 60 |
| agaagttcct cttctgtttc tttgaaggct gccgaaaagc ctttcaaggt tactgtgatt | 120 |
| ggatctggta actggggtac tactattgcc aaggtggttg ccgaaaattg taagggatac | 180 |
| ccagaagttt cgctccaat agtacaaatg tgggtgttcg aagaagagat caatggtgaa | 240 |
| aaattgactg aaatcataaa tactagacat caaaacgtga atacttgcc tggcatcact | 300 |
| ctacccgaca atttggttgc taatccagac ttgattgatt cagtcaagga tgtcgacatc | 360 |
| atcgttttca acattccaca tcaattttg ccccgtatct gtagccaatt gaaaggtcat | 420 |
| gttgattcac acgtcagagc tatctcctgt ctaaagggt tgaagttgg tgctaaaggt | 480 |
| gtccaattgc tatcctctta catcactgag gaactaggta ttcaatgtgg tgctctatct | 540 |

```
ggtgctaaca ttgccaccga agtcgctcaa gaacactggt ctgaaacaac agttgcttac    600
cacattccaa aggatttcag aggcgagggc aaggacgtcg accataaggt tctaaaggcc    660
ttgttccaca gaccttactt ccacgttagt gtcatcgaag atgttgctgg tatctccatc    720
tgtggtgctt tgaagaacgt tgttgcctta ggttgtggtt tcgtcgaagg tctaggctgg    780
ggtaacaacg cttctgctgc catccaaaga gtcggtttgg gtgagatcat cagattcggt    840
caaatgtttt tcccagaatc tagaagaa acatactacc aagagtctgc tggtgttgct     900
gatttgatca ccacctgcgc tggtggtaga aacgtcaagg ttgctaggct aatggctact    960
tctggtaagg acgcctggga atgtgaaaag gagttgttga atggccaatc cgctcaaggt   1020
ttaattacct gcaaagaagt tcacgaatgg ttggaaacat gtggctctgt cgaagacttc   1080
ccattatttg aagccgtata ccaaatcgtt tacaacaact acccaatgaa gaacctgccg   1140
gacatgattg aagaattaga tctacatgaa gattag                             1176
```

<210> SEQ ID NO 11
<211> LENGTH: 332
<212> TYPE: PRT
<213> ORGANISM: Pelodiscus sinensis japonicus

<400> SEQUENCE: 11

```
Met Ser Val Lys Glu Leu Leu Ile Gln Asn Val His Lys Glu His
 1               5                  10                  15

Ser His Ala His Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Arg Gly Glu Met Leu Asp
     50                  55                  60

Leu Gln His Gly Ser Leu Phe Leu Arg Thr Pro Lys Ile Val Ser Gly
 65                  70                  75                  80

Lys Asp Tyr Ser Val Thr Ala His Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asp Cys Met Leu Leu Val Val Ser Asn Pro Val Asp Ile Leu Thr
    130                 135                 140

Tyr Val Ala Trp Lys Ile Ser Gly Phe Pro Lys His Arg Val Ile Gly
145                 150                 155                 160

Ser Gly Cys Asn Leu Asp Ser Ala Arg Phe Arg Tyr Leu Met Gly Glu
                165                 170                 175

Lys Leu Gly Ile His Ser Leu Ser Cys His Gly Trp Ile Ile Gly Glu
            180                 185                 190

His Gly Asp Ser Ser Val Pro Val Trp Ser Gly Val Asn Val Ala Gly
        195                 200                 205

Val Ser Leu Lys Ala Leu Tyr Pro Asp Leu Gly Thr Asp Ala Asp Lys
    210                 215                 220

Glu His Trp Lys Glu Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255
```

Ala Asp Leu Ala Glu Thr Val Met Lys Asn Leu Arg Arg Val His Pro
                260                 265                 270

Ile Ser Thr Met Val Lys Gly Met Tyr Gly Val Ser Ser Asp Val Phe
            275                 280                 285

Leu Ser Val Pro Cys Val Leu Gly Tyr Ala Gly Ile Thr Asp Val Val
        290                 295                 300

Lys Met Thr Leu Lys Ser Glu Glu Glu Lys Leu Arg Lys Ser Ala
305                 310                 315                 320

Asp Thr Leu Trp Gly Ile Gln Lys Glu Leu Gln Phe
                325                 330

<210> SEQ ID NO 12
<211> LENGTH: 332
<212> TYPE: PRT
<213> ORGANISM: Ornithorhynchus anatinus

<400> SEQUENCE: 12

Met Ala Gly Val Lys Glu Gln Leu Ile Gln Asn Leu Leu Lys Glu Glu
1               5                   10                  15

Tyr Ala Pro Gln Asn Lys Ile Thr Val Val Gly Val Gly Ala Val Gly
                20                  25                  30

Met Ala Cys Ala Ile Ser Ile Leu Met Lys Asp Leu Ala Asp Glu Leu
            35                  40                  45

Ala Leu Val Asp Val Ile Glu Asp Lys Leu Lys Gly Glu Met Met Asp
        50                  55                  60

Leu Gln His Gly Ser Leu Phe Leu Arg Thr Pro Lys Ile Val Ser Gly
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Val Val Ser Asn Pro Val Asp Ile Leu Thr
130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Ile His Ser Thr Ser Cys His Gly Trp Val Ile Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Asp Leu Gly Thr Asp Ala Asp Lys
210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Val Lys Asn Leu Arg Arg Val His Pro
            260                 265                 270

Ile Ser Thr Met Ile Lys Gly Leu Tyr Gly Ile Lys Asp Glu Val Phe
        275                 280                 285

Leu Ser Val Pro Cys Val Leu Gly Gln Asn Gly Ile Ser Asp Val Val
290                 295                 300

```
Lys Ile Thr Leu Lys Ser Glu Glu Ala His Leu Lys Lys Ser Ala
305                 310                 315                 320

Asp Thr Leu Trp Gly Ile Gln Lys Glu Leu Gln Phe
                325                 330

<210> SEQ ID NO 13
<211> LENGTH: 332
<212> TYPE: PRT
<213> ORGANISM: Tursiops truncatus

<400> SEQUENCE: 13

Met Ala Thr Val Lys Asp Gln Leu Ile Gln Asn Leu Leu Lys Glu Glu
  1               5                  10                  15

His Val Pro Gln Asn Lys Ile Thr Val Val Gly Val Gly Ala Val Gly
                 20                  25                  30

Met Ala Cys Ala Ile Ser Ile Leu Met Lys Asp Leu Ala Asp Glu Leu
             35                  40                  45

Ala Leu Val Asp Val Ile Glu Asp Lys Leu Lys Gly Glu Met Met Asp
         50                  55                  60

Leu Gln His Gly Ser Leu Phe Leu Arg Thr Pro Lys Ile Val Ser Gly
 65                  70                  75                  80

Lys Asp Tyr Ser Val Thr Ala Asn Ser Lys Leu Val Ile Ile Thr Ala
                 85                  90                  95

Gly Ala Arg Gln Gln Glu Gly Glu Ser Arg Leu Asn Leu Val Gln Arg
            100                 105                 110

Asn Val Asn Ile Phe Lys Phe Ile Val Pro Asn Ile Val Lys Tyr Ser
        115                 120                 125

Pro His Cys Lys Leu Leu Val Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Ile Leu Gly Glu
            180                 185                 190

His Gly Asp Ser Ser Val Pro Val Trp Ser Gly Val Asn Val Ala Gly
        195                 200                 205

Val Ser Leu Lys Asn Leu His Pro Glu Leu Gly Thr Asp Ala Asp Lys
    210                 215                 220

Glu His Trp Lys Ala Ile His Lys Gln Val Val Asp Ser Ala Tyr Glu
225                 230                 235                 240

Val Ile Lys Leu Lys Gly Tyr Thr Ser Trp Ala Val Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Glu Glu Gln Ala Cys Leu Lys Lys Ser Ala
305                 310                 315                 320

Asp Thr Leu Trp Gly Ile Gln Lys Glu Leu Gln Phe
                325                 330
```

<210> SEQ ID NO 14
<211> LENGTH: 332
<212> TYPE: PRT
<213> ORGANISM: Rattus norvegicus

<400> SEQUENCE: 14

Met Ala Ala Leu Lys Asp Gln Leu Ile Val Asn Leu Lys Glu Glu
1               5                   10                  15

Gln Val Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Lys Thr Pro Lys Ile Val Ser Ser
65                  70                  75                  80

Lys Asp Tyr Ser Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Gln Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Val Asn Val Ala Gly
        195                 200                 205

Val Ser Leu Lys Ser Leu Asn Pro Gln Leu Gly Thr Asp Ala Asp Lys
    210                 215                 220

Glu Gln Trp Lys Asp Val His Lys Gln Val Val Asp Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Ile Ser Thr Met Ile Lys Gly Leu Tyr Gly Ile Lys Glu Asp Val Phe
        275                 280                 285

Leu Ser Val Pro Cys Ile Leu Gly Gln Asn Gly Ile Ser Asp Val Val
    290                 295                 300

Lys Val Thr Leu Thr Pro Asp Glu Glu Ala Arg Leu Lys Lys Ser Ala
305                 310                 315                 320

Asp Thr Leu Trp Gly Ile Gln Lys Glu Leu Gln Phe
                325                 330

<210> SEQ ID NO 15
<211> LENGTH: 999
<212> TYPE: DNA
<213> ORGANISM: Pelodiscus sinensis japonicus

<400> SEQUENCE: 15
atgtccgtaa aggaactact tatacaaaac gtccataagg aggagcattc tcacgctcac      60

```
aataagataa cagttgtagg agtaggtgca gtaggtatgg catgtgctat ttcgatatta      120
atgaaagact tggctgatga actagccttg gttgatgtga ttgaggataa gttacgtgga      180
gaaatgttag atttgcaaca tggttcattg ttcttgagaa cccccaaaat tgtctcgggt      240
aaggattatt cagtcactgc tcattctaaa ctggttatca ttacagcagg tgcaagacag      300
caagaagggg agagcagact aaatctggtt caacgtaatg tcaacatctt caagtttatc      360
atcccgaacg tagtaaaata cagtccagac tgcatgttgc ttgttgtgag taatccagtt      420
gacatcttaa cctatgttgc gtggaaaatc agtgggtttc aaaacatag ggtgattggc       480 tcaggatgca accttgatag cgccaggttt aggtatctaa tgggagaaaa attaggtatt      540
cactccttat cttgtcatgg ctggataata ggcgaacatg gtgattcttc ggtacctgtt      600
tggtccgggg ttaatgtggc tggtgttagt ttaaaagcat tatatcctga cctgggtact      660
gatgccgata agaacattg gaaagaagtg cacaaacaag tggttgattc tgcttacgaa       720
gttattaaac ttaagggcta cacttcttgg gctataggtc tatcagtagc tgatttggca      780
gaaaccgtta tgaaaaattt aagaagagtc cacccaattt ccacgatggt caagggtatg      840
tacggtgtta gctctgacgt cttcttatct gttccttgtg ttttgggata tgcgggaatt      900
acagacgtcg tgaagatgac attgaaatca gaggaagagg aaaaactaag aaagtcagcc      960
gatactctgt ggggcattca aaaggaattg cagttttaa                            999

<210> SEQ ID NO 16
<211> LENGTH: 289
<212> TYPE: DNA
<213> ORGANISM: Artificial Sequence
<220> FEATURE:
<223> OTHER INFORMATION: Synthetic CYC promoter

<400> SEQUENCE: 16
atttggcgag cgttggttgg tggatcaagc ccacgcgtag gcaatcctcg agcagatccg       60
ccaggcgtgt atatatagcg tggatggcca ggcaacttta gtgctgacac atacaggcat      120 atatatgt gtgcgacgac acatgatcat atggcatgca tgtgctctgt atgtatataa        180
aactcttgtt ttcttctttt ctctaaatat tctttcctta tacattagga cctttgcagc      240
ataaattact atacttctat agacacgcaa acacaaatac acacactaa                 289

<210> SEQ ID NO 17
<211> LENGTH: 401
<212> TYPE: DNA
<213> ORGANISM: Artificial Sequence
<220> FEATURE:
<223> OTHER INFORMATION: Synthetic TEF promoter

<400> SEQUENCE: 17
atagcttcaa aatgtttcta ctccttttt actcttccag attttctcgg actccgcgca       60
tcgccgtacc acttcaaaac acccaagcac agcatactaa atttcccctc tttcttcctc      120
tagggtgtcg ttaattaccc gtactaaagg tttggaaaag aaaaaagaga ccgcctcgtt      180
tctttttctt cgtcgaaaaa ggcaataaaa atttttatca cgtttctttt tcttgaaaat      240 ttttttttttg attttttttct ctttcgatga cctcccattg atatttaagt taataaacgg    300
tcttcaattt ctcaagtttc agtttcattt tcttgttct attacaactt ttttttacttc     360 ttgctcatta gaaagaaagc atagcaatct aatctaagtt t                         401

<210> SEQ ID NO 18
```

<211> LENGTH: 655
<212> TYPE: DNA
<213> ORGANISM: Artificial Sequence
<220> FEATURE:
<223> OTHER INFORMATION: Synthetic GPD promoter

<400> SEQUENCE: 18

```
agtttatcat tatcaatact cgccatttca aagaatacgt aaataattaa tagtagtgat      60
tttcctaact ttatttagtc aaaaaattag ccttttaatt ctgctgtaac ccgtacatgc     120
ccaaaatagg gggcgggtta cacagaatat ataacatcgt aggtgtctgg gtgaacagtt    180
tattcctggc atccactaaa tataatggag cccgcttttt aagctggcat ccagaaaaaa     240
aaagaatccc agcaccaaaa tattgttttc ttcaccaacc atcagttcat aggtccattc     300
tcttagcgca actacagaga acaggggcac aaacaggcaa aaacgggca caacctcaat      360
ggagtgatgc aacctgcctg gagtaaatga tgacacaagg caattgaccc acgcatgtat     420
ctatctcatt ttcttacacc ttctattacc ttctgctctc tctgatttgg aaaaagctga    480
aaaaaaaggt tgaaaccagt tccctgaaat tattccccta cttgactaat aagtatataa     540
agacggtagg tattgattgt aattctgtaa atctatttct taaacttctt aaattctact    600
tttatagtta gtcttttttt tagttttaaa acaccagaac ttagtttcga cggat         655
```

<210> SEQ ID NO 19
<211> LENGTH: 1468
<212> TYPE: DNA
<213> ORGANISM: Artificial Sequence
<220> FEATURE:
<223> OTHER INFORMATION: Synthetic ADH promoter

<400> SEQUENCE: 19

```
gccgggatcg aagaaatgat ggtaaatgaa ataggaaatc aaggagcatg aaggcaaaag     60
acaaatataa gggtcgaacg aaaaataaag tgaaagtgt tgatatgatg tatttggctt    120
tgcggcgccg aaaaacgag tttacgcaat tgcacaatca tgctgactct gtggcggacc     180
cgcgctcttg ccggcccggc gataacgctg ggcgtgaggc tgtgcccggc ggagttttt     240
gcgcctgcat tttccaaggt ttaccctgcg ctaaggggcg agattggaga agcaataaga    300
atgccggttg gggttgcgat gatgacgacc acgacaactg gtgtcattat ttaagttgcc     360
gaaagaacct gagtgcattt gcaacatgag tatactagaa gaatgagcca agacttgcga    420
gacgcgagtt tgccggtggt gcgaacaata gagcgaccat gaccttgaag gtgagacgcg     480
cataaccgct agagtacttt gaagaggaaa cagcaatagg gttgctacca gtataaatag    540
acaggtacat acaacactgg aaatggttgt ctgtttgagt acgctttcaa ttcatttggg     600
tgtgcacttt attatgttac aatatggaag gaactttac acttctccta tgcacatata    660
ttaattaaag tccaatgcta gtagagaagg ggggtaacac ccctccgcgc tcttttccga    720
ttttttccta aaccgtggaa tatttcggat atccttttgt tgtttccggg tgtacaatat    780
ggacttcctc ttttctggca accaaaccca tacatcggga ttcctataat accttcgttg    840
gtctccctaa catgtaggtg gcggagggga gatatacaat agaacagata ccagacaaga    900
cataatgggc taaacaagac tacaccaatt acactgcctc attgatggtg gtacataacg    960
aactaatact gtagccctag acttgatagc catcatcata tcgaagtttc actaccctttt   1020
ttccatttgc catctattga agtaataata ggcgcatgca acttcttttc tttttttttc   1080
ttttctctct ccccgttgt tgtctcacca tatccgcaat gacaaaaaaa tgatggaaga   1140
cactaaagga aaaaattaac gacaaagaca gcaccaacag atgtcgttgt tccagagctg   1200
```

```
atgaggggta tctcgaagca cacgaaactt tttccttcct tcattcacgc acactactct   1260
ctaatgagca acggtatacg gccttccttc cagttacttg aatttgaaat aaaaaaaagt   1320
ttgctgtctt gctatcaagt ataaatagac ctgcaattat taatcttttg tttcctcgtc   1380
attgttctcg ttccctttct tccttgtttc tttttctgca caatatttca agctatacca   1440
agcatacaat caactccaag ctggccgc                                      1468
```

<210> SEQ ID NO 20
<211> LENGTH: 292
<212> TYPE: DNA
<213> ORGANISM: Artificial Sequence
<220> FEATURE:
<223> OTHER INFORMATION: Synthetic CCW12 promoter

<400> SEQUENCE: 20

```
ttcgcggcca cctacgccgc tatctttgca acaactatct gcgataactc agcaaatttt    60
gcatattcgt gttgcagtat tgcgataatg ggagtcttac ttccaacata acggcagaaa   120
gaaatgtgag aaaattttgc atcctttgcc tccgttcaag tatataaagt cggcatgctt   180
gataatcttt ctttccatcc tacattgttc taattattct tattctcctt tattctttcc   240
taacatacca agaaattaat cttctgtcat tcgcttaaac actatatcaa ta           292
```

<210> SEQ ID NO 21
<211> LENGTH: 252
<212> TYPE: DNA
<213> ORGANISM: Artificial Sequence
<220> FEATURE:
<223> OTHER INFORMATION: Synthetic CYC1 terminator

<400> SEQUENCE: 21

```
tcatgtaatt agttatgtca cgcttacatt cacgccctcc ccccacatcc gctctaaccg    60
aaaaggaagg agttagacaa cctgaagtct aggtccctat ttattttttt atagttatgt   120
tagtattaag aacgttattt atatttcaaa ttttttcttt ttttctgtac agacgcgtgt   180
acgcatgtaa cattatactg aaaaccttgc ttgagaaggt tttgggacgc tcgaaggctt   240
taatttgcgg cc                                                      252
```

<210> SEQ ID NO 22
<211> LENGTH: 59
<212> TYPE: DNA
<213> ORGANISM: Artificial Sequence
<220> FEATURE:
<223> OTHER INFORMATION: Synthetic primer

<400> SEQUENCE: 22

```
gtaggaggtt ttgcactact taacagacaa ataaaacgag cagctgaagc ttcgtacgc    59
```

<210> SEQ ID NO 23
<211> LENGTH: 60
<212> TYPE: DNA
<213> ORGANISM: Artificial Sequence
<220> FEATURE:
<223> OTHER INFORMATION: Synthetic primer

<400> SEQUENCE: 23

```
aggacattcc atcaggcttc caatctaacc ccaaccttgc ataggccact agtggatctg    60
```

<210> SEQ ID NO 24
<211> LENGTH: 21
<212> TYPE: DNA

```
<213> ORGANISM: Artificial Sequence
<220> FEATURE:
<223> OTHER INFORMATION: Synthetic primer

<400> SEQUENCE: 24
ccaggagtta ttaaaagaca g                                           21

<210> SEQ ID NO 25
<211> LENGTH: 18
<212> TYPE: DNA
<213> ORGANISM: Artificial Sequence
<220> FEATURE:
<223> OTHER INFORMATION: Synthetic primer

<400> SEQUENCE: 25
agttatcctt ggatttgg                                               18

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
caattttaga gcagtaggct t                                           21

<210> SEQ ID NO 27
<211> LENGTH: 59
<212> TYPE: DNA
<213> ORGANISM: Artificial Sequence
<220> FEATURE:
<223> OTHER INFORMATION: Synthetic primer

<400> SEQUENCE: 27 gaatttatt cgaacgcata gagtacacac actcaaagga cagctgaagc ttcgtacgc    59

<210> SEQ ID NO 28
<211> LENGTH: 60
<212> TYPE: DNA
<213> ORGANISM: Artificial Sequence
<220> FEATURE:
<223> OTHER INFORMATION: Synthetic primer

<400> SEQUENCE: 28
tccaaaaaaa ccatcgggaa ggtttctttt tagtatctgc ataggccact agtggatctg  60

<210> SEQ ID NO 29
<211> LENGTH: 20
<212> TYPE: DNA
<213> ORGANISM: Artificial Sequence
<220> FEATURE:
<223> OTHER INFORMATION: Synthetic primer

<400> SEQUENCE: 29
ttcctttctt ctcaaacttt                                             20

<210> SEQ ID NO 30
<211> LENGTH: 19
<212> TYPE: DNA
<213> ORGANISM: Artificial Sequence
<220> FEATURE:
<223> OTHER INFORMATION: Synthetic primer

<400> SEQUENCE: 30
tctttactgc gataacggt                                              19
```

<210> SEQ ID NO 31
<211> LENGTH: 31
<212> TYPE: DNA
<213> ORGANISM: Artificial Sequence
<220> FEATURE:
<223> OTHER INFORMATION: Synthetic primer

<400> SEQUENCE: 31
cgagctcttc gcggccacct acgccgctat c         31

<210> SEQ ID NO 32
<211> LENGTH: 32
<212> TYPE: DNA
<213> ORGANISM: Artificial Sequence
<220> FEATURE:
<223> OTHER INFORMATION: Synthetic primer

<400> SEQUENCE: 32
gctctagata ttgatatagt gtttaagcga at        32

<210> SEQ ID NO 33
<211> LENGTH: 27
<212> TYPE: DNA
<213> ORGANISM: Artificial Sequence
<220> FEATURE:
<223> OTHER INFORMATION: Synthetic primer

<400> SEQUENCE: 33
cggccatggc gggagctcgc atgcaag              27

<210> SEQ ID NO 34
<211> LENGTH: 28
<212> TYPE: DNA
<213> ORGANISM: Artificial Sequence
<220> FEATURE:
<223> OTHER INFORMATION: Synthetic primer

<400> SEQUENCE: 34
cgggatatca ctagtgagct cgctccgc             28

<210> SEQ ID NO 35
<211> LENGTH: 2321
<212> TYPE: DNA
<213> ORGANISM: Artificial Sequence
<220> FEATURE:
<223> OTHER INFORMATION: Synthetic HPH cassette

<400> SEQUENCE: 35
gccgggagag ctcgcatgca agtaacctat tcaaagtaat atctcataca tgtttcatga    60
gggtaacaac atgcgactgg gtgagcatat gttccgctga tgtgatgtgc aagataaaca   120
agcaaggcag aaactaactt cttcttcatg taataaacac accccgcgtt tatttaccta   180
tctctaaact tcaacacctt atatcataac taatatttct tgagataagc acactgcacc   240
cataccttcc ttaaaaacgt agcttccagt ttttggtggt tccggcttcc ttcccgattc   300
cgcccgctaa acgcatattt ttgttgcctg gtggcatttg caaaatgcat aacctatgca   360
tttaaaagat tatgtatgct cttctgactt tcgtgtgat gaggctcgtg aaaaaatga   420 ataatttatg aatttgagaa caattttgtg ttgttacggt attttactat ggaataatca   480
atcaattgag gattttatgc aaatatcgtt tgaatatttt tccgacccctt tgagtacttt   540 tcttcataat tgcataatat tgtccgctgc cccttttttct gttagacggt gtcttgatct   600

```
acttgctatc gttcaacacc acctatttt ctaactattt ttttttttagc tcatttgaat    660 cagcttatgg tgatggcaca tttttgcata aacctagctg tcctcgttga acataggaaa    720
aaaaaatata taaacaaggc tctttcactc tccttgcaat cagatttggg tttgttccct    780 ttatttcat atttcttgtc atattccttt ctcaattatt attttctact cataacctca     840
cgcaaaataa cacagtcaaa tcctcgagat gaaaaagcct gaactcaccg cgacgtctgt    900
cgagaagttt ctgatcgaaa agttcgacag cgtctccgac ctgatgcagc tctcggaggg    960
cgaagaatct cgtgctttca gcttcgatgt aggagggcgt ggatatgtcc tgcgggtaaa   1020
tagctgcgcc gatggtttct acaaagatcg ttatgtttat cggcactttg catcggccgc   1080
gctcccgatt ccggaagtgc ttgacattgg ggaattcagc gagagcctga cctattgcat   1140
ctcccgccgt gcacagggtg tcacgttgca agacctgcct gaaaccgaac tgcccgctgt   1200
tctgcagccg gtcgcggagg ccatggatgc gatcgctgcg gccgatctta ccagacgag    1260 cgggttcggc ccattcggac cgcaaggaat cggtcaatac actacatggc gtgatttcat   1320
atgcgcgatt gctgatcccc atgtgtatca ctggcaaact gtgatggacg acaccgtcag   1380
tgcgtccgtc gcgcaggctc tcgatgagct gatgctttgg gccgaggact gccccgaagt   1440
ccggcacctc gtgcacgcgg atttcggctc caacaatgtc ctgacggaca atggccgcat   1500
aacagcggtc attgactgga gcgaggcgat gttcggggat cccaatacag aggtcgccaa   1560
catcttcttc tggaggccgt ggttggcttg tatggagcag cagacgcgct acttcgagcg   1620
gaggcatccg gagcttgcag atcgccgcg gctccgggcg tatatgctcc gcattggtct    1680
tgaccaactc tatcagagct tggttgacgg caatttcgat gatgcagctt gggcgcaggg   1740
tcgatgcgac gcaatcgtcc gatccggagc cgggactgtc gggcgtacac aaatcgcccg   1800
cagaagcgcg gccgtctgga ccgatggctg tgtagaagta ctcgccgata gtggaaaccg   1860
acgccccagc actcgtccgg atcgggagat gggggaggct aactgaggat ccgtagatac   1920
attgatgcta tcaatcaaga gaactggaaa gattgtgtaa ccttgaaaaa cggtgaaact   1980
tacgggtcca agattgtcta cagatttcc tgatttgcca gcttactatc cttcttgaaa    2040
atatgcactc tatatctttt agttcttaat tgcaacacat agatttgctg tataacgaat   2100
tttatgctat ttttttaaatt tggagttcag tgataaaagt gtcacagcga atttcctcac   2160
atgtagggac cgaattgttt acaagttctc tgtaccacca tggagacatc aaaaattgaa   2220
aatctatgga aagatatgga cggtagcaac aagaatatag cacgagccgc ggagcgagct   2280
cggccgcact agtgatatcc cgcggccatg gcggccggga g                       2321
```

<210> SEQ ID NO 36
<211> LENGTH: 18
<212> TYPE: DNA
<213> ORGANISM: Artificial Sequence
<220> FEATURE:
<223> OTHER INFORMATION: Synthetic primer

<400> SEQUENCE: 36
gaaacagcta tgaccatg                                                    18

<210> SEQ ID NO 37
<211> LENGTH: 32
<212> TYPE: DNA
<213> ORGANISM: Artificial Sequence
<220> FEATURE:
<223> OTHER INFORMATION: Synthetic primer

<400> SEQUENCE: 37

```
gacatgacga gctcgaattg ggtaccggcc gc                                    32

<210> SEQ ID NO 38
<211> LENGTH: 4173
<212> TYPE: DNA
<213> ORGANISM: Artificial Sequence
<220> FEATURE:
<223> OTHER INFORMATION: Synthetic pUC57-Ura3HA vector

<400> SEQUENCE: 38
gatgacggtg aaaacctctg acacatgcag ctcccggaga cggtcacagc ttgtctgtaa     60
gcggatgccg ggagcagaca gcccgtcag ggcgcgtcag cgggtgttgg cgggtgtcgg    120
ggctggctta actatgcggc atcagagcag attgtactga gagtgcacca tatgcggtgt    180
gaaataccgc acagatgcgt aaggagaaaa taccgcatca ggcgccattc gccattcagg    240
ctgcgcaact gttgggaagg gcgatcggtg cgggcctctt cgctattacg ccagctggcg    300 aaaggggat gtgctgcaag gcgattaagt tgggtaacgc cagggttttc ccagtcacga    360
cgttgtaaaa cgacggccag tgaattcgag ctcggtacct cgcgaatgca tctagatatc    420
ggatcccgac gagctgcacc gcggtggcgg ccgtatcttt acccatacg atgttcctga    480 ctatgcgggc tatccctatg acgtcccgga ctatgcagga tcctatccat atgacgttcc    540
agattacgct gctcagtgcg gccgcctgag agtgcaccat accacagctt ttcaattcaa    600
ttcatcattt ttttttttatt cttttttttg atttcggttt ctttgaaatt tttttgattc    660
ggtaatctcc gaacagaagg aagaacgaag gaaggagcac agacttagat tggtatatat    720
acgcatatgt agtgttgaag aaacatgaaa ttgcccagta ttcttaaccc aactgcacag    780
aacaaaaacc tgcaggaaac gaagataaat catgtcgaaa gctacatata aggaacgtgc    840
tgctactcat cctagtcctg ttgctgccaa gctatttaat atcatgcacg aaaagcaaac    900
aaacttgtgt gcttcattgg atgttcgtac caccaaggaa ttactggagt tagttgaagc    960
attaggtccc aaaatttgtt tactaaaaac acatgtggat atcttgactg attttttccat   1020 ggagggcaca gttaagccgc taaaggcatt atccgccaag tacaattttt tactcttcga   1080
agacagaaaa tttgctgaca ttggtaatac agtcaaattg cagtactctg cggtgtata    1140 cagaatagca gaatgggcag acattacgaa tgcacacggt gtggtgggcc caggtattgt   1200
tagcggtttg aagcaggcgg cagaagaagt aacaaaggaa cctagaggcc ttttgatgtt   1260
agcagaattg tcatgcaagg gctccctatc tactggagaa tatactaagg gtactgttga   1320
cattgcgaag agcgacaaag attttgttat cggctttatt gctcaaagag acatgggtgg   1380
aagagatgaa ggttacgatt ggttgattat gacacccggt gtgggtttag atgacaaggg   1440
agacgcattg gtcaacagt atagaaccgt ggatgatgtg gtctctacag gatctgacat   1500
tattattgtt ggaagaggac tatttgcaaa gggaagggat gctaaggtag agggtgaacg   1560
ttacagaaaa gcaggctggg aagcatattt gagaagatgc ggccagcaaa actaaaaaac   1620
tgtattataa gtaaatgcat gtatactaaa ctcacaaatt agagcttcaa tttaattata   1680
tcagttatta ccctatgcgg tgtgaaatac cgcacagatg cgtaaggaga aaataccgca   1740
tcaggaaatt gtagcggccg cgaatttgag cttatctttt acccatacga tgttcctgac   1800
tatgcgggct atccctatga cgtcccggac tatgcaggat cctatccata tgacgttcca   1860
gattacgcta ctagcggggg gcccggtgac gggcccgtcg actgcagagg cctgcatgca   1920
agcttggcgt aatcatggtc atagctgttt cctgtgtgaa attgttatcc gctcacaatt   1980
```

| | | |
|---|---|---|
| ccacacaaca tacgagccgg aagcataaag tgtaaagcct ggggtgccta atgagtgagc | 2040 |
| taactcacat taattgcgtt gcgctcactg cccgctttcc agtcgggaaa cctgtcgtgc | 2100 |
| cagctgcatt aatgaatcgg ccaacgcgcg gggagaggcg gtttgcgtat tgggcgctct | 2160 |
| tccgcttcct cgctcactga ctcgctgcgc tcggtcgttc ggctgcggcg agcggtatca | 2220 |
| gctcactcaa aggcggtaat acggttatcc acagaatcag gggataacgc aggaaagaac | 2280 |
| atgtgagcaa aaggccagca aaaggccagg aaccgtaaaa aggccgcgtt gctggcgttt | 2340 |
| ttccataggc tccgcccccc tgacgagcat cacaaaaatc gacgctcaag tcagaggtgg | 2400 |
| cgaaacccga caggactata aagataccag gcgtttcccc ctggaagctc cctcgtgcgc | 2460 |
| tctcctgttc cgaccctgcc gcttaccgga tacctgtccg cctttctccc ttcgggaagc | 2520 |
| gtggcgcttt ctcatagctc acgctgtagg tatctcagtt cggtgtaggt cgttcgctcc | 2580 |
| aagctgggct gtgtgcacga accccccgtt cagcccgacc gctgcgcctt atccggtaac | 2640 |
| tatcgtcttg agtccaaccc ggtaagacac gacttatcgc cactggcagc agccactggt | 2700 |
| aacaggatta gcagagcgag gtatgtaggc ggtgctacag agttcttgaa gtggtggcct | 2760 |
| aactacggct acactagaag aacagtattt ggtatctgcg ctctgctgaa gccagttacc | 2820 |
| ttcggaaaaa gagttggtag ctcttgatcc ggcaaacaaa ccaccgctgg tagcggtggt | 2880 |
| ttttttgttt gcaagcagca gattacgcgc agaaaaaaag gatctcaaga agatcctttg | 2940 |
| atcttttcta cggggtctga cgctcagtgg aacgaaaact cacgttaagg gattttggtc | 3000 |
| atgagattat caaaaaggat cttcacctag atccttttaa attaaaaatg aagttttaaa | 3060 |
| tcaatctaaa gtatatatga gtaaacttgg tctgacagtt accaatgctt aatcagtgag | 3120 |
| gcacctatct cagcgatctg tctatttcgt tcatccatag ttgcctgact ccccgtcgtg | 3180 |
| tagataacta cgatacggga gggcttacca tctggcccca gtgctgcaat gataccgcga | 3240 |
| gacccacgct caccggctcc agatttatca gcaataaacc agccagccgg aagggccgag | 3300 |
| cgcagaagtg gtcctgcaac tttatccgcc tccatccagt ctattaattg ttgccgggaa | 3360 |
| gctagagtaa gtagttcgcc agttaatagt ttgcgcaacg ttgttgccat tgctacaggc | 3420 |
| atcgtggtgt cacgctcgtc gtttggtatg gcttcattca gctccggttc caacgatca | 3480 |
| aggcgagtta catgatcccc catgttgtgc aaaaaagcgg ttagctcctt cggtcctccg | 3540 |
| atcgttgtca gaagtaagtt ggccgcagtg ttatcactca tggttatggc agcactgcat | 3600 |
| aattctctta ctgtcatgcc atccgtaaga tgcttttctg tgactggtga gtactcaacc | 3660 |
| aagtcattct gagaatagtg tatgcggcga ccgagttgct cttgcccggc gtcaatacgg | 3720 |
| gataataccg cgccacatag cagaacttta aaagtgctca tcattggaaa acgttcttcg | 3780 |
| gggcgaaaac tctcaaggat cttaccgctg ttgagatcca gttcgatgta acccactcgt | 3840 |
| gcacccaact gatcttcagc atcttttact ttcaccagcg tttctgggtg agcaaaaaca | 3900 |
| ggaaggcaaa atgccgcaaa aaagggaata agggcgacac ggaaatgttg aatactcata | 3960 |
| ctcttccttt ttcaatatta ttgaagcatt tatcagggtt attgtctcat gagcggatac | 4020 |
| atatttgaat gtatttagaa aaataaacaa ataggggttc cgcgcacatt tccccgaaaa | 4080 |
| gtgccacctg acgtctaaga aaccattatt atcatgacat taacctataa aaataggcgt | 4140 |
| atcacgaggc cctttcgtct cgcgcgtttc ggt | 4173 |

<210> SEQ ID NO 39
<211> LENGTH: 62
<212> TYPE: DNA
<213> ORGANISM: Artificial Sequence

```
<220> FEATURE:
<223> OTHER INFORMATION: Synthetic primer

<400> SEQUENCE: 39
gcttataaaa ctttaactaa taattagaga ttaaatcgct taaggtttcc cgactggaaa    60
gc                                                                   62

<210> SEQ ID NO 40
<211> LENGTH: 64
<212> TYPE: DNA
<213> ORGANISM: Artificial Sequence
<220> FEATURE:
<223> OTHER INFORMATION: Synthetic primer

<400> SEQUENCE: 40
ctactcataa cctcacgcaa aataacacag tcaaatcaat caaaccagtc acgacgttgt    60
aaaa                                                                 64

<210> SEQ ID NO 41
<211> LENGTH: 20
<212> TYPE: DNA
<213> ORGANISM: Artificial Sequence
<220> FEATURE:
<223> OTHER INFORMATION: Synthetic primer

<400> SEQUENCE: 41
ggacgtaaag ggtagcctcc                                                20

<210> SEQ ID NO 42
<211> LENGTH: 22
<212> TYPE: DNA
<213> ORGANISM: Artificial Sequence
<220> FEATURE:
<223> OTHER INFORMATION: Synthetic primer

<400> SEQUENCE: 42
gaagcggacc cagacttaag cc                                             22

<210> SEQ ID NO 43
<211> LENGTH: 65
<212> TYPE: DNA
<213> ORGANISM: Artificial Sequence
<220> FEATURE:
<223> OTHER INFORMATION: Synthetic primer

<400> SEQUENCE: 43
ccgaaatgat tcccttttcct gcacaacacg agatctttca cgcatccagt cacgacgttg    60
taaaa                                                                65

<210> SEQ ID NO 44
<211> LENGTH: 64
<212> TYPE: DNA
<213> ORGANISM: Artificial Sequence
<220> FEATURE:
<223> OTHER INFORMATION: Synthetic primer

<400> SEQUENCE: 44
aaagtagcct taaagctagg ctataatcat gcatcctcaa attctaggtt tcccgacgga    60
aagc                                                                 64

<210> SEQ ID NO 45
<211> LENGTH: 25
<212> TYPE: DNA
```

```
<213> ORGANISM: Artificial Sequence
<220> FEATURE:
<223> OTHER INFORMATION: Synthetic primer

<400> SEQUENCE: 45
cgcaagaacg tagtatccac atgcc                                              25

<210> SEQ ID NO 46
<211> LENGTH: 21
<212> TYPE: DNA
<213> ORGANISM: Artificial Sequence
<220> FEATURE:
<223> OTHER INFORMATION: Synthetic primer

<400> SEQUENCE: 46
ggatatttac agaacgatgc g                                                  21

<210> SEQ ID NO 47
<211> LENGTH: 70
<212> TYPE: DNA
<213> ORGANISM: Artificial Sequence
<220> FEATURE:
<223> OTHER INFORMATION: Synthetic primer

<400> SEQUENCE: 47
ccctatgtct ctggccgatc acgcgccatt gtccctcaga aacaaatcaa ccagtcacga        60
cgttgtaaaa                                                               70

<210> SEQ ID NO 48
<211> LENGTH: 70
<212> TYPE: DNA
<213> ORGANISM: Artificial Sequence
<220> FEATURE:
<223> OTHER INFORMATION: Synthetic primer

<400> SEQUENCE: 48
tagaagcaac tgtgccgaca gcctctgaat gagtggtgtt gtaaccaccc aggtttcccg        60
actggaaagc                                                               70

<210> SEQ ID NO 49
<211> LENGTH: 25
<212> TYPE: DNA
<213> ORGANISM: Artificial Sequence
<220> FEATURE:
<223> OTHER INFORMATION: Synthetic primer

<400> SEQUENCE: 49
tcaatgagac tgttgtcctc ctact                                              25

<210> SEQ ID NO 50
<211> LENGTH: 24
<212> TYPE: DNA
<213> ORGANISM: Artificial Sequence
<220> FEATURE:
<223> OTHER INFORMATION: Synthetic primer

<400> SEQUENCE: 50
tacatccttg tcgagccttg ggca                                               24
```